United States Patent
Haas et al.

(10) Patent No.: US 9,920,334 B2
(45) Date of Patent: *Mar. 20, 2018

(54) AEROBIC METHOD OF PRODUCING ALCOHOLS

(71) Applicant: Evonik Degussa GmbH, Essen (DE)

(72) Inventors: Thomas Haas, Muenster (DE); Thomas Buelter, Duisburg (DE); Martin Demler, Dorsten (DE); Simon Beck, Muenster (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/009,453

(22) Filed: Jan. 28, 2016

(65) Prior Publication Data

US 2016/0215304 A1 Jul. 28, 2016

(30) Foreign Application Priority Data

Jan. 28, 2015 (EP) ..................................... 15152866

(51) Int. Cl.
| | |
|---|---|
| *C12N 1/14* | (2006.01) |
| *C12P 7/06* | (2006.01) |
| *C12N 1/20* | (2006.01) |
| *C12P 7/02* | (2006.01) |
| *C12R 1/145* | (2006.01) |
| *C12P 7/04* | (2006.01) |
| *C12P 7/14* | (2006.01) |

(52) U.S. Cl.
CPC ................ *C12P 7/065* (2013.01); *C12N 1/20* (2013.01); *C12P 7/02* (2013.01); *C12P 7/04* (2013.01); *C12P 7/14* (2013.01); *C12R 1/145* (2013.01); *Y02E 50/17* (2013.01)

(58) Field of Classification Search
CPC ...................................... C12N 1/14; C12P 7/06
See application file for complete search history.

(56) References Cited

U.S. PATENT DOCUMENTS

| | | |
|---|---|---|
| 2007/0275447 A1 | 11/2007 | Lewis et al. |
| 2008/0057554 A1 | 3/2008 | Huhnke et al. |
| 2010/0203606 A1 | 8/2010 | Huhnke et al. |
| 2012/0009638 A1* | 1/2012 | Tsai ....................... C12M 21/12 435/140 |

FOREIGN PATENT DOCUMENTS

| | | |
|---|---|---|
| WO | WO 2008/028055 A2 | 3/2008 |
| WO | WO 2008/028055 A3 | 3/2008 |

OTHER PUBLICATIONS

U.S. Appl. No. 14/400,379, filed May 8, 2013, 2015/0125912, Thomas Haas, et al.
U.S. Appl. No. 14/380,483, filed Feb. 22, 2013, 2015/0254747, Yvonne Schiemann, et al.
U.S. Appl. No. 14/363,165, filed Nov. 22, 2012, 2015/0044744, Jan Pfeffer, et al.
U.S. Appl. No. 14/367,610, filed Dec. 14, 2012, 2015/0275245, Thomas Haas, et al.
Extended European Search Report dated Aug. 10, 2015 in Patent Application No. 15152866.8.
A. L. Brioukhanov, et al., "Aerotolerance of Strictly Anaerobic Microorganisms and Factors of Defense Against Oxidative Stress: A Review" Applied Biochemistry and Microbiology, vol. 43, No. 6, XP055198053, 2007, pp. 567-582.
Deshai Botheju, et al., "Oxygen Effects in Anaerobic Digestion—A Review" The Open Waste Management Journal, vol. 4, No. 1, XP055119737, 2011, pp. 1-19.
Bettina Schiel-Bengelsdorf, et al., "Pathway engineering and synthetic biology using acetogens" Federation of European Biochemical Societies (FEBS) Letters, vol. 586, No. 15, XP028400698; 2012, pp. 2191-2198.
Kan Liu, et al., "Mixed culture syngas fermentation and conversion of carboxylic acids into alcohols" Bioresource Technology, vol. 152, XP055110212, 2014, pp. 337-346.
Jose M. Perez, et al., "Biocatalytic Reduction of Short-Chain Carboxylic Acids Into Their Corresponding Alcohols With Syngas Fermentation" Biotechnology and Bioengineering, vol. 110, No. 4, XP002694318, Apr. 2013, pp. 1066-1077.

\* cited by examiner

*Primary Examiner* — Maryam Monshipouri
(74) *Attorney, Agent, or Firm* — Oblon, McClelland, Maier & Neustadt, L.L.P.

(57) ABSTRACT

A reaction mixture for producing ethanol and/or acetate from a carbon source in aerobic conditions, wherein the mixture comprises
  a first acetogenic microorganism in an exponential growth phase;
  free oxygen; and
  a second acetogenic microorganism in a stationary phase
  wherein the first and second acetogenic microorganism is capable of converting the carbon source to the acetate and/or ethanol.

13 Claims, No Drawings

AEROBIC METHOD OF PRODUCING ALCOHOLS

BACKGROUND OF THE INVENTION

Field of the Invention

The present invention relates to a reaction mixture and a biotechnological method of producing alcohols including higher alcohols from a carbon source in aerobic conditions. In particular, the mixture and method relates to a biotechnological production of at least one alcohol in the presence of oxygen and young cells.

Discussion of the Background

Biotechnological methods of producing alcohols, particularly ethanol are well known in the art. Especially the use of acetogenic bacteria on various carbon sources to produce ethanol and/or acetate is well known. However, in most cases, the production of alcohols can only be successfully carried out in the absence of oxygen. This phenomenon is confirmed at least by Brioukhanov, 2006, Imlay, 2006, Lan, 2013 and the like where it is shown that acetogenic bacteria do not successfully produce ethanol in aerobic conditions. Therefore, in the current methods known in the art, carbon substrates comprising oxygen, such as waste gases from steel mills are first processed to remove the oxygen before they are introduced to the acetogenic cells for ethanol and/or acetate production. The oxygen separation step makes the process more expensive and time consuming. Further, there may be some loss in the raw materials during this step of separation.

There is thus a need in the art for a means of producing ethanol and/or acetate in the presence of oxygen. Ethanol may then be used as a raw material for production of higher carbon compounds such as alcohol, acids and the like.

For example, butanol and higher alcohols have several uses including being used as fuel. For example, butanol in the future can replace gasoline as the energy contents of the two fuels are nearly the same. Further, butanol has several other superior properties as an alternative fuel when compared to ethanol. These include butanol having higher energy content, butanol being less "evaporative" than ethanol or gasoline and butanol being easily transportable compared to ethanol. For these reasons and more, there is already an existing potential market for butanol and/or related higher alcohols. Butanol and other higher alcohols are also used as industrial solvents.

Currently, butanol and other higher alcohols are primarily manufactured from petroleum. These compounds are obtained by cracking gasoline or petroleum which is bad for the environment. Also, since the costs for these starting materials will be linked to the price of petroleum, with the expected increase in petroleum prices in the future, butanol and other higher alcohol prices may also increase relative to the increase in the petroleum prices.

Historically (1900s-1950s), biobutanol was manufactured from corn and molasses in a fermentation process that also produced acetone and ethanol and was known as an ABE (acetone, butanol, ethanol) fermentation typically with certain butanol-producing bacteria such as *Clostridium acetobutylicum* and *Clostridium beijerinckii*. This method has recently gained popularity again with renewed interest in green energy. However, the "cornstarch butanol production" process requires a number of energy-consuming steps including agricultural corn-crop cultivation, corn-grain harvesting, corn-grain starch processing, and starch-to-sugar-to-butanol fermentation. The "cornstarch butanol production" process could also probably cost nearly as much energy as the energy value of its product butanol.

The Alfol® Alcohol Process is a method used to producing higher alcohols from ethylene using an organoaluminium catalyst. The reaction produces linear long chain primary alcohols ($C_2$-$C_{28}$). The process uses an aluminum catalyst to oligomerize ethylene and allow the resulting alkyl group to be oxygenated. However, this method yields a wide spectrum of alcohols and the distribution pattern is maintained. This constant pattern limits the ability of the producer to make only the specific alcohol range that is in highest demand or has the best economic value. Also, the gases needed in the reaction have to be very clean and a distinct composition of the gases is needed for the reaction to be successfully carried out.

WO2009100434 also describes an indirect method of producing butanol and hexanol from a carbohydrate. The method includes a homoacetogenic fermentation to produce an acetic acid intermediate which is then chemically converted to ethanol. The ethanol and a remaining portion of the acetic acid intermediate are then used as a substrate in an acidogenic fermentation to produce butyric and caproic acid intermediates which are then chemically converted to butanol and hexanol. However, this method uses expensive raw material carbohydrates and has two additional process steps, the formation of the esters and the chemical hydrogenation of the esters which make the method not only longer but also results in loss of useful material along the way.

Perez, J. M., 2012 discloses a method of converting short-chain carboxylic acids into their corresponding alcohols in the presence of syngas with the use of *Clostridium ljungdahlii*. However, short-chain carboxylic acids have to be added as a substrate for the conversion to the corresponding higher alcohol.

The currently available methods of higher alcohol production thus has limitations in mass transfer of the gaseous substrates into fermentation broth, lower productivity, and lower concentrations of end products, resulting in higher energy costs for product purification.

SUMMARY OF THE INVENTION

Accordingly, it is desirable to find more sustainable raw materials, other than purely petroleum based or corn based sources, as starting materials for butanol and other higher alcohol production via biotechnological means which also cause less damage to the environment. In particular, there is a need for a simple and efficient one-pot biotechnological production of butanol and other higher alcohols from sustainable raw material.

The present invention solves the problems mentioned above by providing a means of producing ethanol and higher alcohols in aerobic conditions by introducing acetogenic cells in the exponential/log growth phase to an aqueous medium comprising a carbon source and oxygen. The concentration of these acetogenic cells in the exponential/log growth phase may be maintained by any means known in the art provided there is oxygen constantly present in the aqueous medium. The oxygen may be present in the aqueous medium at a concentration of at least 5 ppm.

DETAILED DESCRIPTION OF THE INVENTION

In one aspect of the present invention, there is provided a reaction mixture for producing ethanol and/or acetate from a carbon source in aerobic conditions, wherein the mixture comprises a first acetogenic microorganism in an exponential growth phase;

free oxygen; and a second acetogenic microorganism in a post exponential phase wherein the first and second acetogenic microorganism is capable of converting the carbon source to the acetate and/or ethanol.

In particular, the second acetogenic microorganism in a post exponential phase may be in the stationary phase of the cell. The acetogenic cells in the log phase allow for any other acetogenic cells in the aqueous medium to produce acetate and/or ethanol in the presence of oxygen. The concentration of acetogenic cells in the log phase may be maintained in the reaction mixture. Therefore, at any point in time in the reaction, the reaction mixture comprises acetogenic cells in the log phase and acetogenic cells in another growth phase, for example in the stationary phase.

A skilled person would understand the different growth phases of microorganisms and the methods to measure them and identify them. In particular, most microorganisms in batch culture, may be found in at least four different growth phases; namely they are: lag phase (A), log phase or exponential phase (B), stationary phase (C), and death phase (D). The log phase may be further divided into the early log phase and mid to late log/exponential phase. The stationary phase may also be further distinguished into the early stationary phase and the stationary phase. For example, Cotter, J. L., 2009, Najafpour, G., 2006, Younesi, H., 2005, and Köpke, M., 2009 disclose different growth phases of acetogenic bacteria. In particular, the growth phase of cells may be measured using methods taught at least in Shuler M L, 1992 and Fuchs G., 2007.

The lag phase is the phase immediately after inoculation of the cells into a fresh medium, the population remains temporarily unchanged. Although there is no apparent cell division occurring, the cells may be growing in volume or mass, synthesizing enzymes, proteins, RNA, etc., and increasing in metabolic activity. The length of the lag phase may be dependent on a wide variety of factors including the size of the inoculum; time necessary to recover from physical damage or shock in the transfer; time required for synthesis of essential coenzymes or division factors; and time required for synthesis of new (inducible) enzymes that are necessary to metabolize the substrates present in the medium.

The exponential (log) phase of growth is a pattern of balanced growth wherein all the cells are dividing regularly by binary fission, and are growing by geometric progression. The cells divide at a constant rate depending upon the composition of the growth medium and the conditions of incubation. The rate of exponential growth of a bacterial culture is expressed as generation time, also the doubling time of the bacterial population. Generation time (G) is defined as the time (t) per generation (n=number of generations). Hence, G=t/n is the equation from which calculations of generation time derive. The exponential phase may be divided into the (i) early log phase and (ii) mid to late log/exponential phase. A skilled person may easily identify when a microorganism, particularly an acetogenic bacteria, enters the log phase. For example, the method of calculating the growth rate of acetogenic bacteria to determine if they are in the log phase may be done using the method taught at least in Henstra A. M., 2007. In particular, the microorganism in the exponential growth phase according to any aspect of the present invention may include cells in the early log phase and mid to late log/exponential phase.

The stationary phase is the phase where exponential growth ends as exponential growth cannot be continued forever in a batch culture (e.g. a closed system such as a test tube or flask). Population growth is limited by one of three factors: 1. exhaustion of available nutrients; 2. accumulation of inhibitory metabolites or end products; 3. exhaustion of space, in this case called a lack of "biological space". During the stationary phase, if viable cells are being counted, it cannot be determined whether some cells are dying and an equal number of cells are dividing, or the population of cells has simply stopped growing and dividing. The stationary phase, like the lag phase, is not necessarily a period of quiescence. Bacteria that produce secondary metabolites, such as antibiotics, do so during the stationary phase of the growth cycle (Secondary metabolites are defined as metabolites produced after the active stage of growth).

The death phase follows the stationary phase. During the death phase, the number of viable cells decreases geometrically (exponentially), essentially the reverse of growth during the log phase.

In one example, where $O_2$ is present in the reaction mixture according to any aspect of the present invention, the first acetogenic bacteria may be in an exponential growth phase and the other acetogenic bacteria may be in any other growth phase in the lifecycle of an acetogenic microorganism. In particular, according to any aspect of the present invention, the acetogenic bacteria in the reaction mixture may comprise one acetogenic bacteria in an exponential growth phase and another in the stationary phase. In the presence of oxygen, without the presence of the acetogenic bacteria in an exponential growth, the acetogenic bacteria in the stationary phase may not be capable of producing acetate and/or ethanol. This phenomenon is confirmed at least by Brioukhanov, 2006, Imlay, 2006, Lan, 2013 and the like. The inventors thus surprisingly found that in the presence of acetogenic bacteria in an exponential growth, the acetogenic bacteria in any growth phase may aerobically respire and produce acetate and/or ethanol at more than or equal to the amounts produced when the reaction mixture was absent of oxygen. In one example, the acetogenic bacteria in the exponential growth phase may be capable of removing the free oxygen from the reaction mixture, providing a suitable environment (with no free oxygen) for the acetogenic bacteria in any growth phase to metabolise the carbon substrate to produce acetate and/or ethanol.

In another example, the aqueous medium may already comprise acetogenic bacteria in any growth phase, particularly in the stationary phase, in the presence of a carbon source. In this example, there may be oxygen present in the carbon source supplied to the aqueous medium or in the aqueous medium itself. In the presence of oxygen, the acetogenic bacteria may be inactive and not produce acetate and/or ethanol prior to the addition of the acetogenic bacteria in the exponential growth phase. In this very example, the acetogenic bacteria in the exponential growth phase may be added to the aqueous medium. The inactive acetogenic bacteria already found in the aqueous medium may then be activated and may start producing acetate and/or ethanol.

In a further example, the acetogenic bacteria in any growth phase may be first mixed with the acetogenic bacteria in the exponential growth phase and then the carbon source and/or oxygen added.

According to any aspect of the present invention, a microorganism in the exponential growth phase grown in the presence of oxygen may result in the microorganism gaining an adaptation to grow and metabolise in the presence of oxygen. In particular, the microorganism may be capable of removing the oxygen from the environment surrounding the microorganism. This newly acquired adaptation allows for the acetogenic bacteria in the exponential growth phase to rid the environment of oxygen and therefore produce acetate and ethanol from the carbon source. In particular, the acetogenic bacteria with the newly acquired adaptation allows for the bacteria to convert the carbon source to acetate and/or ethanol.

In one example, the acetogenic bacteria in the reaction mixture according to any aspect of the present impression may comprise a combination of cells: cells in the log phase and cells in the stationary phase. In the method according to any aspect of the present invention the acetogenic cells in the log phase may comprise a growing rate selected from the group consisting of 0.01 to 2 h$^{-1}$, 0.01 to 1 h$^{-1}$, 0.05 to 1 h$^{-1}$, 0.05 to 2 h$^{-1}$ 0.05 to 0.5 h$^{-1}$ and the like. In one example, the OD$_{600}$ of the cells of the log phase acetogenic cells in the reaction mixture may be selected from the range consisting of 0.001 to 2, 0.01 to 2, 0.1 to 1, 0.1 to 0.5 and the like. A skilled person would be able to use any method known in the art to measure the OD$_{600}$ and determine the growth rate of the cells in the reaction mixture and/or to be added in the reaction mixture. For example, Koch (1994) may be used. In particular, bacterial growth can be determined and monitored using different methods. One of the most common is a turbidity measurement, which relies upon the optical density (OD) of bacteria in suspension and uses a spectrophotometer. The OD may be measured at 600 nm using a UV spectrometer.

In order to maintain the concentration of the first and second acetogenic bacteria in the reaction mixture, a skilled person may be capable of extracting a sample at fixed time points to measure the OD$_{600}$, pH, concentration of oxygen and concentration of ethanol and/or higher alcohols formed. The skilled person would then be able to add the necessary component(s) to maintain the concentration of first and second acetogenic bacteria in the reaction mixture and to ensure an optimum environment is maintained for the production of ethanol and/or acetate.

The term "acetogenic bacteria" as used herein refers to a microorganism which is able to perform the Wood-Ljungdahl pathway and thus is able to convert CO, CO$_2$ and/or hydrogen to acetate. These microorganisms include microorganisms which in their wild-type form do not have a Wood-Ljungdahl pathway, but have acquired this trait as a result of genetic modification. Such microorganisms include but are not limited to *E. coli* cells. These microorganisms may be also known as carboxydotrophic bacteria. Currently, 21 different genera of the acetogenic bacteria are known in the art (Drake et al., 2006), and these may also include some *clostridia* (Drake & Kusel, 2005). These bacteria are able to use carbon dioxide or carbon monoxide as a carbon source with hydrogen as an energy source (Wood, 1991). Further, alcohols, aldehydes, carboxylic acids as well as numerous hexoses may also be used as a carbon source (Drake et al., 2004). The reductive pathway that leads to the formation of acetate is referred to as acetyl-CoA or Wood-Ljungdahl pathway.

In particular, the acetogenic bacteria may be selected from the group consisting of *Acetoanaerobium notera* (ATCC 35199), *Acetonema longum* (DSM 6540), *Acetobacterium carbinolicum* (DSM 2925), *Acetobacterium malicum* (DSM 4132), *Acetobacterium* species no. 446 (Morinaga et al., 1990, *J. Biotechnol.*, Vol. 14, p. 187-194), *Acetobacterium wieringae* (DSM 1911), *Acetobacterium woodii* (DSM 1030), *Alkalibaculum bacchi* (DSM 22112), *Archaeoglobus fulgidus* (DSM 4304), *Blautia producta* (DSM 2950, formerly *Ruminococcus productus*, formerly *Peptostreptococcus productus*), *Butyribacterium methylotrophicum* (DSM 3468), *Clostridium aceticum* (DSM 1496), *Clostridium autoethanogenum* (DSM 10061, DSM 19630 and DSM 23693), *Clostridium carboxidivorans* (DSM 15243), *Clostridium coskatii* (ATCC no. PTA-10522), *Clostridium drakei* (ATCC BA-623), *Clostridium formicoaceticum* (DSM 92), *Clostridium glycolicum* (DSM 1288), *Clostridium ljungdahlii* (DSM 13528), *Clostridium ljungdahlii* C-01 (ATCC 55988), *Clostridium ljungdahlii* ERI-2 (ATCC 55380), *Clostridium ljungdahlii* O-52 (ATCC 55989), *Clostridium mayombei* (DSM 6539), *Clostridium methoxybenzovorans* (DSM 12182), *Clostridium ragsdalei* (DSM 15248), *Clostridium scatologenes* (DSM 757), *Clostridium* species ATCC 29797 (Schmidt et al., 1986, *Chem. Eng. Commun.*, Vol. 45, p. 61-73), *Desulfotomaculum kuznetsovii* (DSM 6115), *Desulfotomaculum thermobezoicum* subsp. *thermosyntrophicum* (DSM 14055), *Eubacterium limosum* (DSM 20543), *Methanosarcina acetivorans* C2A (DSM 2834), *Moorella* sp. HUC22-1 (Sakai et al., 2004, *Biotechnol. Let.*, Vol. 29, p. 1607-1612), *Moorella thermoacetica* (DSM 521, formerly *Clostridium thermoaceticum*), *Moorella thermoautotrophica* (DSM 1974), *Oxobacter pfennigii* (DSM 322), *Sporomusa aerivorans* (DSM 13326), *Sporomusa ovata* (DSM 2662), *Sporomusa silvacetica* (DSM 10669), *Sporomusa sphaeroides* (DSM 2875), *Sporomusa termitida* (DSM 4440) and *Thermoanaerobacter kivui* (DSM 2030, formerly *Acetogenium kivui*). More in particular, the strain ATCC BAA-624 of *Clostridium carboxidivorans* may be used. Even more in particular, the bacterial strain labelled "P7" and "P11" of *Clostridium carboxidivorans* as described for example in U.S. 2007/0275447 and U.S. 2008/0057554 may be used.

Another particularly suitable bacterium may be *Clostridium ljungdahlii*. In particular, strains selected from the group consisting of *Clostridium ljungdahlii* PETC, *Clostridium ljungdahlii* ERI2, *Clostridium ljungdahlii* COL and *Clostridium ljungdahlii* O-52 may be used in the conversion of synthesis gas to hexanoic acid. These strains for example are described in WO 98/00558, WO 00/68407, ATCC 49587, ATCC 55988 and ATCC 55989. The first and second acetogenic bacteria used according to any aspect of the present invention may be the same or different bacteria. For example, in one reaction mixture the first acetogenic bacteria may be *Clostridium ljungdahlii* in the log phase and the second acetogenic bacteria may be *Clostridium ljungdahlii* in the stationary phase. In another example, in the reaction mixture the first acetogenic bacteria may be *Clostridium ljungdahlii* in the log phase and the second acetogenic bacteria may be *Clostridium carboxidivorans* in the stationary phase. In another example, the acetogenic bacteria selected for the first organism may be *Clostridium autoethanogenum*.

In the reaction mixture according to any aspect of the present invention, there may be oxygen present. It is advantageous to incorporate O$_2$ in the reaction mixture and/or gas flow being supplied to the reaction mixture as most waste gases including synthesis gas comprises oxygen in small or large amounts. It is difficult and costly to remove this oxygen prior to using synthesis gas as a carbon source for production of higher alcohols. The method according to any aspect of the present invention allows the production of at least one higher alcohol without the need to first remove any trace of oxygen from the carbon source. This allows for time and money to be saved.

More in particular, the O$_2$ concentration in the gas flow may be may be present at less than 1% by volume of the total amount of gas in the gas flow. In particular, the oxygen may be present at a concentration range of 0.000005 to 2% by volume, at a range of 0.00005 to 2% by volume, 0.0005 to 2% by volume, 0.005 to 2% by volume, 0.05 to 2% by volume, 0.00005 to 1.5% by volume, 0.0005 to 1.5% by volume, 0.005 to 1.5% by volume, 0.05 to 1.5% by volume, 0.5 to 1.5% by volume, 0.00005 to 1% by volume, 0.0005 to 1% by volume, 0.005 to 1% by volume, 0.05 to 1% by volume, 0.5 to 1% by volume, 0.55 to 1% by volume, 0.60 to 1% by volume, particularly at a range of 0.60 to 1.5%, 0.65 to 1%, and 0.70 to 1% by volume. In particular, the acetogenic microorganism is particularly suitable when the proportion of $O_2$ in the gas phase/flow is about 0.00005, 0.0005, 0.005, 0.05, 0.15, 0.5, 0.6, 0.7, 0.8, 0.9, 1, 1.5, 2% by volume in relation to the volume of the gas in the gas flow. A skilled person would be able to use any one of the methods known in the art to measure the volume concentration of oxygen in the gas flow. In particular, the volume of oxygen may be measured using any method known in the art. In one example, a gas phase concentration of oxygen may be measured by a trace oxygen dipping probe from PreSens Precision Sensing GmbH. Oxygen concentration may be measured by fluorescence quenching, where the degree of quenching correlates to the partial pressure of oxygen in the gas phase. Even more in particular, the first and second microorganisms according to any aspect of the present invention are capable of working optimally in the aqueous medium when the oxygen is supplied by a gas flow with concentration of oxygen of less than 1% by volume of the total gas, in about 0.015% by volume of the total volume of gas in the gas flow supplied to the reaction mixture.

According to any aspect of the present invention, the aerobic conditions in which the carbon source is converted to ethanol and/or acetate in the reaction mixture refers to gas surrounding the reaction mixture. The gas may comprise at least 1% by volume of the total gas of oxygen and other gases including carbon sources such as CO, $CO_2$ and the like.

The aqueous medium according to any aspect of the present invention may comprise oxygen. The oxygen may be dissolved in the medium by any means known in the art. In particular, the oxygen may be present at 0.5 mg/L in the absence of cells. In particular, the dissolved concentration of free oxygen in the aqueous medium may at least be 0.01 mg/L. In another example, the dissolved oxygen may be about 0.01, 0.02, 0.03, 0.04, 0.05, 0.1, 0.2, 0.3, 0.4, 0.5 mg/L. In particular, the dissolved oxygen concentration may be 0.01-0.5 mg/L, 0.01-0.4 mg/L, 0.01-0.3 mg/L, 0.01-0.1 mg/L. In particular, the oxygen may be provided to the aqueous medium in a continuous gas flow. More in particular, the aqueous medium may comprise oxygen and a carbon source comprising CO and/or $CO_2$. More in particular, the oxygen and a carbon source comprising CO and/or $CO_2$ is provided to the aqueous medium in a continuous gas flow. Even more in particular, the continuous gas flow comprises synthesis gas and oxygen. In one example, both gases are part of the same flow/stream. In another example, each gas is a separate flow/stream provided to the aqueous medium. These gases may be divided for example using separate nozzles that open up into the aqueous medium, fits, membranes within the pipe supplying the gas into the aqueous medium and the like. The oxygen may be free oxygen. According to any aspect of the present invention, 'a reaction mixture comprising free oxygen' refers to the reaction mixture comprising elemental oxygen in the form of $O_2$. The $O_2$ may be dissolved oxygen in the reaction mixture. In particular, the dissolved oxygen may be in the concentration of ≥5 ppm (0.000005% vol; $5\times10^{-6}$). A skilled person may be capable of using any method known in the art to measure the concentration of dissolved oxygen. In one example, the dissolved oxygen may be measured by Oxygen Dipping Probes (Type PSt6 from PreSens Precision Sensing GmbH, Regensburg, Germany).

According to any aspect of the present invention, the reaction mixture further comprises
  a third microorganism capable of carrying out the ethanol carboxylate fermentation pathway and converting acetate and/or ethanol to form an acid; and
wherein the first and/or second acetogenic microorganism is capable of converting the acid to a corresponding higher alcohol.

In one example, the acetogenic bacteria may be used in conjunction with a second microorganism that may be capable of carrying out the ethanol-carboxylate fermentation pathway. In one example, both the first and second acetogenic bacteria and a third microorganism that may be capable of carrying out the ethanol-carboxylate fermentation pathway may be used to produce a higher acid from the carbon source. The acid may then be converted to the corresponding higher alcohol selected from the group consisting of butanol, pentanol, hexanol, octanol, nonanol, decanol and the like. In one example the higher alcohol may be selected from the group consisting of 1-butanol, 2-methyl-1-butanol, isobutanol, 3-methyl-1-butanol, 1-hexanol, 1-octanol, 1-pentanol, 1-heptanol, 3-methyl-1-pentanol, 4-methyl-1-hexanol, 5-methyl-1-heptanol, 4-methyl-1-pentanol, 5-methyl-1-hexanol, 6-methyl-1-heptanol and combinations thereof.

In one example, the ethanol and/or acetate may be converted to the corresponding higher acid in the presence of the third microorganism capable of carrying out the ethanol-carboxylate fermentation pathway. The ethanol-carboxylate fermentation pathway is described in detail at least in Seedorf, H., et al., 2008. In particular, the third organism may be selected from the group consisting of *Clostridium kluyveri, C. Carboxidivorans* and the like. These third microorganisms include microorganisms which in their wild-type form do not have an ethanol-carboxylate fermentation pathway, but have acquired this trait as a result of genetic modification. In particular, the third microorganism may be *Clostridium kluyveri*.

In another example, the third microorganism may be a wild type organism that expresses at least one enzyme selected from the group consisting of $E_1$ to $E_{11}$, wherein $E_1$ is an alcohol dehydrogenase (adh), $E_2$ is an acetaldehyde dehydrogenase (ald), $E_3$ is an acetoacetyl-CoA thiolase (thl), $E_4$ is a 3-hydroxybutyryl-CoA dehydrogenase (hbd), $E_5$ is a 3-hydroxybutyryl-CoA dehydratase (crt), $E_6$ is a butyryl-CoA dehydrogenase (bcd), $E_7$ is an electron transfer flavoprotein subunit (etf), $E_8$ is a coenzyme A transferase (cat), $E_9$ is an acetate kinase (ack), $E_{10}$ is phosphotransacetylase (pta) and $E_{11}$ is a transhydrogenase. In particular, the wild type third microorganism according to any aspect of the present invention may express at least $E_2$, $E_3$ and $E_4$. Even more in particular, the wild type third microorganism according to any aspect of the present invention may express at least $E_4$.

In another example, the third microorganism according to any aspect of the present invention may be a genetically modified organism that has increased expression relative to the wild type microorganism of at least one enzyme selected $E_1$ to $E_{11}$ wherein $E_1$ is an alcohol dehydrogenase (adh), $E_2$ is an acetaldehyde dehydrogenase (ald), $E_3$ is an acetoacetyl-CoA thiolase (thl), $E_4$ is a 3-hydroxybutyryl-CoA dehydrogenase (hbd), $E_5$ is a 3-hydroxybutyryl-CoA dehydratase (crt), $E_6$ is a butyryl-CoA dehydrogenase (bcd), $E_7$ is an electron transfer flavoprotein subunit (etf), $E_8$ is a coenzyme A transferase (cat), $E_9$ is an acetate kinase (ack) $E_{10}$ is phosphotransacetylase (pta) and $E_{11}$ is a transhydrogenase. In particular, the genetically modified third microorganism according to any aspect of the present invention may express at least enzymes $E_2$, $E_3$ and $E_4$. Even more in particular, the genetically modified third microorganism according to any aspect of the present invention may express at least $E_4$. The enzymes $E_1$ to $E_{11}$ may be isolated from *Clostridium kluyveri*. A skilled person may be capable of measuring the activity of each of these enzymes using methods known in the art. In particular, the activity of enzymes $E_1$ and $E_2$ may be measured using the assays taught at least in Hillmer P., 1972, Lurz R., 1979; the activity of enzyme $E_2$ may also be measured using the assay taught in Smith L. T., 1980; the activity of enzymes $E_3$ and $E_4$ may be measured using the assays taught at least in Sliwkowski M. X., 1984; the activity of $E_4$ may also be measured using the assay taught in Madan, V. K., 1972; the activity of $E_5$ may also be measured using the assay taught in Bartsch, R. G., 1961; the activity of enzymes $E_6$ and $E_7$ may be measured using the assay taught in Li, F., 2008; the activity of $E_7$ may also be measured using the assay taught in Chowdhury, 2013; the activity of $E_8$ may be measured using the assay taught in Stadman, 1953; the activity of $E_9$ may be measured using the assay taught in Winzer, K., 1997; the activity of $E_{10}$ may be measured using the assay taught in Smith L. T., 1976; and the activity of $E_{11}$ may be measured using the assay taught in Wang S, 2010.

According to any aspect of the present invention, the first, second and/or third microorganism may be a genetically modified microorganism. The genetically modified cell or microorganism may be genetically different from the wild type cell or microorganism. The genetic difference between the genetically modified microorganism according to any aspect of the present invention and the wild type microorganism may be in the presence of a complete gene, amino acid, nucleotide etc. in the genetically modified microorganism that may be absent in the wild type microorganism. In one example, the genetically modified microorganism according to any aspect of the present invention may comprise enzymes that enable the microorganism to produce at least one carboxylic acid. The wild type microorganism relative to the genetically modified microorganism according to any aspect of the present invention may have none or no detectable activity of the enzymes that enable the genetically modified microorganism to produce at least one carboxylic acid. As used herein, the term 'genetically modified microorganism' may be used interchangeably with the term 'genetically modified cell'. The genetic modification according to any aspect of the present invention may be carried out on the cell of the microorganism.

The phrase "wild type" as used herein in conjunction with a cell or microorganism may denote a cell with a genome make-up that is in a form as seen naturally in the wild. The term may be applicable for both the whole cell and for individual genes. The term "wild type" therefore does not include such cells or such genes where the gene sequences have been altered at least partially by man using recombinant methods.

A skilled person would be able to use any method known in the art to genetically modify a cell or microorganism. According to any aspect of the present invention, the genetically modified cell may be genetically modified so that in a defined time interval, within 2 hours, in particular within 8 hours or 24 hours, it forms at least twice, especially at least 10 times, at least 100 times, at least 1000 times or at least 10000 times more carboxylic acid and/or the respective carboxylic acid ester than the wild-type cell. The increase in product formation can be determined for example by cultivating the cell according to any aspect of the present invention and the wild-type cell each separately under the same conditions (same cell density, same nutrient medium, same culture conditions) for a specified time interval in a suitable nutrient medium and then determining the amount of target product (carboxylic acid) in the nutrient medium.

In another example, an acid may be produced from the carbon source by any method disclosed in Steinbusch, 2011, Zhang, 2013, Van Eerten-Jansen, M. C. A. A, 2013, Ding H. et al, 2010, Barker H. A., 1949, Stadtman E. R., 1950, Bornstein B. T., et al., 1948 and the like. Even more in particular, the acid may be produced from the carbon source in the presence of at least *Clostridium kluyveri*.

Even more in particular, according to any aspect of the present invention, the acid is produced in the presence of at least one acetogenic microorganism in two different growth phases and *Clostridium kluyveri*. In one example, the acetogenic microorganism may be *Clostridium ljungdahlii* or *Clostridium ragsdahlei*. The newly formed acid may be converted to a corresponding higher alcohol in the presence of alcohol. The third microorganism selected from the group consisting of *Clostridium kluyveri*, and *C. Carboxidivorans* may convert the acetate and/or ethanol to form the newly formed acid. As mentioned earlier, it is advantageous for this process to be carried out in the presence of $O_2$ (i.e. to include $O_2$ in the reaction mixture) as most waste gases including synthesis gas comprises oxygen in small or large amounts. This reaction mixture allows for a method of producing higher alcohols from waste gases without having to go through and extra expensive step of extracting oxygen first.

The reaction mixture may comprise the two/three microorganisms in a homogenous mixture. The term 'homogeneous mixture' as used herein refers to a mixture of the microorganisms distributed spatially uniformly in a medium. In particular, the mixture may comprise at least two microorganisms, the two acetogenic microorganisms in different growth phases distributed evenly in an aqueous medium. In one example, there may be approximately equal numbers of the two microorganisms in the mixture. In another example, there may be more of the acetogenic microorganism in the stationary compared to the acetogenic microorganism in the log phase in the mixture. In yet another example, there may be more of the acetogenic microorganism in the log phase compared to the acetogenic microorganism in the stationary phase mixture. In all the possible examples, the microorganisms are in a single homogenous mixture where they are uniformly distributed throughout the mixture. The 'aqueous medium' as used herein may be used interchangeably with the term 'reaction mixture'.

The term "acetate" as used herein, refers to both acetic acid and salts thereof, which results inevitably, because as known in the art, since the microorganisms work in an aqueous environment, and there is always a balance between salt and acid present.

The term "second microorganism" or "third microorganism", refers to a microorganism that is different from "the first microorganism" according to any aspect of the present invention.

In one example, the first and second microorganism may be present in a first fermenter and the third microorganism in a second fermenter. In fermenter 1, the first and second microorganisms come in contact with the carbon source to produce acetate and/or ethanol. Ethanol and/or acetate may then be brought into contact with a third microorganism in fermenter 2 to produce at least one acid. The acid may then be fed back into fermenter 1 to produce at least one alcohol. A cycle may be created wherein the acetate and/or ethanol produced in fermenter 1 may be regularly fed into fermenter 2, the acetate and/or ethanol in fermenter 2 may be converted to at least one acid and the acid in fermenter 2 fed back into fermenter 1.

Similarly, in fermenter 1 the first and second microorganism may come in contact with the carbon source comprising CO to produce acetate and/or ethanol. Ethanol and/or acetate may then be brought into contact with a third microorganism in fermenter 2 to produce at least one acid. The acid may then be optionally extracted and fed back into fermenter 1 to convert the acid to the desired higher alcohol. A cycle may be created wherein the acetate and/or ethanol produced in fermenter 1 may be regularly fed into fermenter 2, the acetate and/or ethanol in fermenter 2 may be converted to at least one acid and the acid in fermenter 2 fed back into fermenter 1. CO fed into fermenter 1 may be transferred into fermenter 2 together with the acetate and/or ethanol. No special extraction method may be needed as the third microorganism has surprisingly been found to convert acetate and/or ethanol to at least one acid in the presence of CO.

In another example, the media is being recycled between fermenters 1 and 2. Therefore, the ethanol and/or acetate produced in fermenter 1 may be fed into fermenter 2 and the acid produced in fermenter 2 may be fed back into fermenter 1. In the process of recycling the media, CO from fermenter 1 may be introduced into fermenter 2. Also, the acids produced in fermenter 2 may be consequently reintroduced into fermenter 1. The third microorganisms in fermenter 2 may be able to continue producing acids from acetate and ethanol in the presence of the CO recycled from fermenter 1 into fermenter 2. The accumulated alcohols in fermenters 1 and 2 may then be extracted by means known in the art.

In a further example, there may be three containers present to carry out the method according to any aspect of the present invention. The first and second microorganism may be present in a first fermenter, the third microorganism in a second fermenter and a third fermenter with the first and second microorganisms. In fermenter 1, the first and second microorganisms come in contact with the carbon source to produce acetate and/or ethanol. Ethanol and/or acetate may then be brought into contact with a third microorganism in fermenter 2 to produce at least one acid. The acid may then be fed into fermenter 3 to produce at least one alcohol.

In the production of the acid and/or higher alcohol from the carbon source a combination of bacteria may be used. There may be more than one acetogenic bacteria present in combination with one or more third microorganisms. In another example, there may be more than one type of acetogenic bacteria present and only one type of third microorganism. In yet another example, there may be more than one third microorganism present in combination with only one acetogenic bacteria.

The term 'about' as used herein refers to a variation within 20 percent. In particular, the term "about" as used herein refers to +/−20%, more in particular, +/−10%, even more in particular, +/−5% of a given measurement or value.

All percentages (%) are, unless otherwise specified, volume percent.

The carbon source used according to any aspect of the present invention comprises carbon dioxide and/or carbon monoxide. A skilled person would understand that many possible sources for the provision of CO and/or $CO_2$ as a carbon source exist. It can be seen that in practice, as the carbon source according to any aspect of the present invention any gas or any gas mixture can be used which is able to supply the microorganisms with sufficient amounts of carbon, so that acetate and/or ethanol, may be formed from the source of CO and/or $CO_2$.

Generally, for the mixed culture according to any aspect of the present invention the carbon source comprises at least 50% by volume, at least 70% by volume, particularly at least 90% by volume of CO and/or $CO_2$, wherein the percentages by volume–% relate to all carbon sources that are available to the first microorganism in the mixed culture.

In the mixed culture according to any aspect of the present invention, the carbon material source may be provided. Examples of carbon sources in gas forms include exhaust gases such as synthesis gas, flue gas and petroleum refinery gases produced by yeast fermentation or clostridial fermentation. These exhaust gases are formed from the gasification of cellulose-containing materials or coal gasification. In one example, these exhaust gases may not necessarily be produced as by-products of other processes but can specifically be produced for use with the mixed culture according to any aspect of the present invention.

According to any aspect of the present invention, the carbon source may be synthesis gas. Synthesis gas can for example be produced as a by-product of coal gasification. Accordingly, the microorganism of the mixed culture according to any aspect of the present invention may be capable of converting a substance which is a waste product into a valuable resource. In another example, synthesis gas may be a by-product of gasification of widely available, low-cost agricultural raw materials for use with the mixed culture of the present invention to produce at least ethanol and/or one higher alcohol.

There are numerous examples of raw materials that can be converted into synthesis gas, as almost all forms of vegetation can be used for this purpose. In particular, raw materials are selected from the group consisting of perennial grasses such as miscanthus, corn residues, processing waste such as sawdust and the like.

In general, synthesis gas may be obtained in a gasification apparatus of dried biomass, mainly through pyrolysis, partial oxidation and steam reforming, wherein the primary products of the synthesis gas are CO, $H_2$ and $CO_2$. Syngas may also be a product of electrolysis of $CO_2$. A skilled person would understand the suitable conditions to carry out electrolysis of $CO_2$ to produce syngas comprising CO in a desired amount.

Usually, a portion of the synthesis gas obtained from the gasification process is first processed in order to optimize product yields, and to avoid formation of tar. Cracking of the undesired tar and CO in the synthesis gas may be carried out using lime and/or dolomite. These processes are described in detail in for example, Reed, 1981.

Mixtures of sources can be used as a carbon source.

According to any aspect of the present invention, a reducing agent, for example hydrogen may be supplied together with the carbon source. In particular, this hydrogen may be supplied when the C and/or $CO_2$ is supplied and/or used. In one example, the hydrogen gas is part of the synthesis gas present according to any aspect of the present invention. In another example, where the hydrogen gas in the synthesis gas is insufficient for the method of the present invention, additional hydrogen gas may be supplied.

A skilled person would understand the other conditions necessary to carry out the method according to any aspect of the present invention. In particular, the conditions in the container (e.g. fermenter) may be varied depending on the first and second microorganisms used. The varying of the conditions to be suitable for the optimal functioning of the microorganisms is within the knowledge of a skilled person.

In one example, the method according to any aspect of the present invention may be carried out in an aqueous medium with a pH between 5 and 8, 5.5 and 7. The pressure may be between 1 and 10 bar.

An advantage of the present invention may be that much more favorable $CO_2/CO$ mixtures of raw materials can be used. These various sources include natural gas, biogas, coal, oil, plant residues and the like. Another advantage of the method may be the high carbon yield. This is made possible by the return of formed $CO_2$. Namely, the $CO_2$ can be reacted in the first stage back to acetic acid.

Another advantage may lie in greater flexibility with regard to the fermentation conditions used, as any acetogenic and any microorganism capable of carrying out the ethanol-carboxylate fermentation pathway may be used in combination for the actual production of higher alcohols. Another advantage of the present invention may be that since the third microorganism may function and/or produce an acid from the acetate and/or ethanol in the presence of CO, both the first, second and third microorganisms may be present in a homogenous mixture for the production of higher alcohols from a carbon source comprising CO. This feature of the third microorganism enables the production of higher alcohols from a carbon source like CO to be a one step process making the process more efficient and the yield greater. Surprisingly, because of this advantage of the third microorganism, the one-step procedure for making higher alcohols may be carried out in a single fermenter without an intermediate separation step. There may also be an increased concentration of the final product using this one step procedure. This is surprising as Baffert C., 2011 and Thauer, R. K., 1973 both teach that hydrogenases were inhibited in the presence of CO. For this reason and more WO2013/167663 comprises a step of separation between (a) a step of forming acetate and/or ethanol from CO and/or $CO_2$ in the presence of an acetogenic organism and (b) a step of forming a hydrocarbon comprising at least one oxygen atom (e.g. hexanoic acid) in the presence of a second microorganism. The ability to produce an alcohol, in particular one which comprises at least 6 carbon atoms, in a one pot synthesis from CO according to any aspect of the present invention is thus a surprising result. In any case, even if steps (a) and (b) are carried out in two separate steps (i.e. two separate containers), there may not be a need for any specific extraction method to remove all traces of CO for both the first and third microorganism to function.

As can be seen in the examples, the presence of CO allows for at least butanol and hexanol to be produced in the method according to any aspect of the present invention wherein the carbon source comprises at least CO.

According to any aspect of the present invention, the carbon source comprises CO. The carbon source comprising CO may be converted to at least one acid in the presence of at least the first and second acetogenic microorganism and a third microorganism capable of carrying out the ethanol-carboxylate fermentation pathway under aerobic conditions. In particular, the acid may comprise 4 or more carbon atoms. More in particular, the acid formed may be selected from the group consisting of butanoic acid, pentanoic acid, hexanoic acid, heptanoic acid, octanoic acid, nonanoic acid, decanoic acid and the like. In particular, the carbon source comprising CO in the presence of the first and second acetogenic bacteria may result in the production of ethanol and/or acetic acid.

In particular, the CO may be provided to the aqueous medium in a continuous gas flow. The CO concentration in the gas flow may be present at least 2% by volume of the volume of the total amount of gas in the gas flow. In particular, the CO may be present at a concentration range of 2 to 99% by volume, at a range of 2 to 95% by volume, 5 to 95% by volume, 10 to 90% by volume, 15 to 85% by volume, particularly at a range of 20 to 80% by volume. More in particular, the concentration of CO may be about 24% by volume. Gas phase concentration of carbon monoxide in the carbon source may be measured using at least a gas chromatograph GC 6890N of Agilent Technologies Inc. with an thermal conductivity detector.

In particular, the aqueous medium may comprise a carbon source comprising CO and/or $CO_2$. More in particular, the carbon source comprising CO and/or $CO_2$ is provided to the aqueous medium in a continuous gas flow. Even more in particular, the continuous gas flow comprises synthesis gas. In one example, the gases are part of the same flow/stream. In another example, each gas is a separate flow/stream provided to the aqueous medium. These gases may be divided for example using separate nozzles that open up into the aqueous medium, frits, membranes within the pipe supplying the gas into the aqueous medium and the like.

In one example according to any aspect of the present invention, the carbon source is synthesis gas and the carbon source may be blended with the oxygen gas before being supplied into the aqueous medium. This blending step may improve the efficiency and the production of higher alcohols in the reaction. The overall efficiency, alcohol productivity and/or overall carbon capture of the method of the present invention may be dependent on the stoichiometry of the $CO_2$, CO, $H_2$ and $O_2$ in the continuous gas flow. The continuous gas flows applied may be of composition $O_2$, $CO_2$ and $H_2$. In particular, in the continuous gas flow, concentration range of $O_2$ may be within 0.000005% to 1% by volume, $CO/CO_2$ about 10-50%, in particular 33% by volume and $H_2$ would be within 44% to 84%, in particular, 64 to 66.04% by volume. More in particular, the concentration of gases in the continuous gas flow may be 0.15% by volume of $O_2$, 32% by volume of $CO/CO_2$ and 64% by volume of $H_2$. In another example, the continuous gas flow can also comprise inert gases like $N_2$, up to a $N_2$ concentration of 50% by volume.

A skilled person would understand that it may be necessary to monitor the composition and flow rates of the streams at relevant intervals. Control of the composition of the stream can be achieved by varying the proportions of the constituent streams to achieve a target or desirable composition. The composition and flow rate of the blended stream can be monitored by any means known in the art. In one example, the system is adapted to continuously monitor the flow rates and compositions of at least two streams and combine them to produce a single blended substrate stream in a continuous gas flow of optimal composition, and means for passing the optimised substrate stream to the mixed culture according to any aspect of the present invention.

In particular, the reaction mixture according to any aspect of the present invention (i.e. mixture of the first microorganism—the acetogenic organism in log phase, the second microorganism—the acetogenic organism in stationary phase, the carbon source in the presence of oxygen can be employed in any known bioreactor or fermenter to carry out any aspect of the present invention. The reaction mixture may further comprise a third microorganism to result in higher alcohols being produced in the fermenter.

'Higher alcohols' as used herein refers to alcohols that contain 4 to 10 carbon atoms and may be somewhat viscous, or oily, and have heavier fruity odours. Higher alcohols may include but are not limited to butanol, pentanol, hexanol, heptanol, octanol, nonanol, decanol and the like. More in particular, the higher alcohol may be selected from the group consisting of 1-butanol, 2-methyl-1-butanol, isobutanol, 3-methyl-1-butanol, 1-hexanol, 1-octanol, 1-pentanol, 1-heptanol, 3-methyl-1-pentanol, 4-methyl-1-hexanol, 5-methyl-1-heptanol, 4-methyl-1-pentanol, 5-methyl-1-hexanol, 6-methyl-1-heptanol and combinations thereof.

According to any aspect of the present invention, the 'corresponding higher alcohol' refers to an alcohol with the same number of carbon atoms as that of the acid from which the corresponding higher alcohol is formed. For example, butanoic acid may be converted to the corresponding alcohol-butanol; hexanoic acid may be converted to the corresponding alcohol-hexanol; heptanoic acid may be converted to the corresponding alcohol-heptanol; octanoic acid may be converted to the corresponding alcohol-octanol; nonanoic acid may be converted to the corresponding alcohol-nonanol; decanoic acid may be converted to the corresponding alcohol-decanol and the like.

The method according to any aspect of the present invention may further comprise the step of extracting the higher alcohol produced. A skilled person will know the means to do so based on the methods known in the art.

According to another aspect of the present invention, a method of producing ethanol and/or acetate from a carbon source in aerobic conditions, the method comprising (a) contacting a reaction mixture comprising a first acetogenic microorganism in an exponential growth phase;

free oxygen; and a second acetogenic microorganism in a stationary phase wherein the first and second acetogenic microorganism is capable of converting the carbon source to the acetate and/or ethanol.

According to another aspect of the present invention, a method of producing at least one higher alcohol from a carbon source in aerobic conditions, the method comprising (a) contacting a reaction mixture according to any aspect of the present invention with a carbon source in aerobic conditions.

Having generally described this invention, a further understanding can be obtained by reference to certain specific examples which are provided herein for purposes of illustration only, and are not intended to be limiting unless otherwise specified.

EXAMPLES

The foregoing describes preferred embodiments, which, as will be understood by those skilled in the art, may be subject to variations or modifications in design, construction or operation without departing from the scope of the claims. These variations, for instance, are intended to be covered by the scope of the claims.

Example 1

Production of Acetate and Ethanol with *Clostridium ljungdahlii* from Synthesis Gas Without Oxygen In this example, *C. ljungdahlii* was anaerobically cultivated in complex medium with synthesis gas, consisting of $H_2$ and $CO_2$ in the absence of oxygen in order to produce acetate and ethanol. For cell culture of *C. ljungdahlii* 2 mL Cryoculture was cultured anaerobically in 200 ml of medium (ATCC1754 medium: pH 6.0; 20 g/L MES; 1 g/L yeast extract, 0.8 g/L NaCl, 1 g/L $NH_4Cl$, 0.1 g/L KCl, 0.1 g/L $KH_2PO_4$, 0.2 g/L $MgSO_4 \times 7\ H_2O$; 0.02 g/L $CaCl_2\ 2H_2O$; 20 mg/L nitrilotriacetic acid 10 mg/L $MnSO_4 \times H_2O$; 8 mg/L $(NH_4)_2Fe(SO_4)_2 \times 6\ H_2O$; 2 mg/L $CoCl_2 \times 6\ H_2O$; 2 mg/L $ZnSO_4 \times 7\ H_2O$; 0.2 mg/L $CuCl_2 \times 2\ H_2O$; 0.2 mg/L $Na_2MoO_4 \times 2\ H_2O$; 0.2 mg/L $NiCl_2 \times 6\ H_2O$; 0.2 mg/L $Na_2SeO_4$; 0.2 mg/L $Na_2WO_4 \times 2\ H_2O$; 20 µg/L d-Biotin, 20 µg/L folic acid, 100 g/L pyridoxine-HC1; 50 µg/L thiamine-HCl×H$_2$O; 50 µg/L riboflavin; 50 µg/L nicotinic acid, 50 µg/L Ca-pantothenate; 1 µg/L vitamin B12; 50 µg/L p-aminobenzoate; 50 µg/L lipoic acid, approximately 67.5 mg/L NaOH) with about 400 mg/L L-cysteine hydrochloride and 400 mg/L $Na_2S \times 9H_2O$. Cultivation was carried chemolithoautotrophically in a flameproof 1 L glass bottle with a premixed gas mixture composed of 67% $H_2$, 33% $CO_2$ in an open water bath shaker at 37° C., 150 rpm and a fumigation of 1-3 L/h for 161 h. The gas entry into the medium was carried out by a filter with a pore size of 10 microns, and was mounted in the middle of the reactor, at a gassing tube. The cells were centrifuged, washed with 10 ml ATCC medium and centrifuged again.

For the preculture many washed cells from the growth culture of *C. ljungdahlii* were transferred into 200 mL of ATCC medium with about 400 mg/L L-cysteine hydrochloride and grown to an $OD_{600}$ of 0.12. Cultivation was carried out in a pressure-resistant 500 ml glass bottle with a premixed gas mixture composed of 67% $H_2$, 33% $CO_2$, in an open water bath shaker at 37° C., 150 rpm and with aeration of 3 L/h for 65 h. The gas entry into the medium was carried out by a filter with a pore size of 10 microns, which was placed in the middle of the reactors. The cells were centrifuged, washed with 10 ml of production buffer (pH 6.2; 0.5 g/L of KOH, aerated for 1 h with a premixed gas mixture of 67% $H_2$, 33% $CO_2$ at 1 L/hr) washed and centrifuged again.

For the production culture many of washed cells from the preculture of *C. ljungdahlii* were transferred into 200 mL of ATCC medium with about 400 mg/L L-cysteine hydrochloride and grown to an $OD_{600}$ of 0.2. Cultivation was carried out in a pressure-resistant 500 ml glass bottle with a premixed gas mixture composed of 67% $H_2$, 33% $CO_2$, in an open water bath shaker at 37° C., 150 rpm and with aeration of 3 L/h for 118 h. The gas entry into the medium was carried out by a filter with a pore size of 10 microns, which was placed in the middle of the reactors. When the pH fell below 5.0, 1 ml of a 140 g/l KOH solution was added. When sampling each 5 ml sample was removed for determination of $OD_{600}$, pH and the product range. The determination of the product concentration was performed by semi-quantitative 1H-NMR spectroscopy. As an internal quantification standard sodium trimethylsilylpropionate served (T (M) SP).

Over the culturing period of 118 h, the cell density in the production culture remained constant, recognizable by a stagnant $OD_{600}$ of 0.2, corresponding to a growth rate of µ=0 hr$^{-1}$. The concentration of acetate increased significantly at the same time from 4 mg/L to 3194 mg/L and the concentration of ethanol from 17 mg/L to 108 mg/L.

Example 2

No Production of Acetate and Ethanol with *Clostridium ljungdahlii* from Synthesis Gas Comprising $CO_2$ and $H_2$ with Oxygen

*C. ljungdahlii* was cultivated in complex medium with synthesis gas and oxygen. *C. ljungdahlii* was first cultured in the presence of synthesis gas consisting of $H_2$ and $CO_2$ in the absence of oxygen in order to produce acetate and ethanol. For the cultivation, the cells were grown in pressure-resistant glass bottles that could be sealed airtight with a butyl rubber stopper. All steps in which *C. ljungdahlii* cells were involved were carried out under anaerobic conditions.

For cell culture of *C. ljungdahlii* 2 mL Cryoculture was cultured anaerobically in 200 ml of medium (ATCC1754 medium: pH 6.0; 20 g/L MES; 1 g/L yeast extract, 0.8 g/L NaCl, 1 g/L NH$_4$Cl, 0.1 g/L KCl, 0.1 g/L KH$_2$PO$_4$, 0.2 g/L MgSO$_4$×7 H$_2$O; 0.02 g/L CaCl$_2$×2H$_2$O; 20 mg/L nitrilotriacetic acid 10 mg/L MnSO$_4$×H$_2$O; 8 mg/L (NH$_4$)$_2$Fe(SO$_4$)$_2$×6 H$_2$O; 2 mg/L CoCl$_2$×6 H$_2$O; 2 mg/L ZnSO$_4$×7 H$_2$O; 0.2 mg/L CuCl$_2$×2 H$_2$O; 0.2 mg/L Na$_2$MoO$_4$×2 H$_2$O; 0.2 mg/L NiCl$_2$×6 H$_2$O; 0.2 mg/L Na$_2$SeO$_4$; 0.2 mg/L Na$_2$WO$_4$×2 H$_2$O; 20 µg/L d-Biotin, 20 µg/L folic acid, 100 g/L pyridoxine-HCl; 50 µg/L thiamine-HCl×H$_2$O; 50 µg/L riboflavin; 50 µg/L nicotinic acid, 50 µg/L Ca-pantothenate; 1 µg/L vitamin B12; 50 µg/L p-aminobenzoate; 50 µg/L lipoic acid, approximately 67.5 mg/L NaOH) with about 400 mg/L L-cysteine hydrochloride and 400 mg/L Na$_2$S×9H$_2$O. Cultivation was carried chemolithoautotrophically in a flameproof 1 L glass bottle with a premixed gas mixture composed of 67% H$_2$, 33% CO$_2$ in an open water bath shaker at 37° C., 150 rpm and a fumigation of 1-3 L/h for 161 h. The gas entry into the medium was carried out by a filter with a pore size of 10 microns, and was mounted in the middle of the reactor, at a gassing tube. The cells were centrifuged, washed with 10 ml ATCC medium and centrifuged again.

For the preculture many washed cells from the growth culture of *C. ljungdahlii* were transferred into 200 mL of ATCC medium with about 400 mg/L L-cysteine hydrochloride and grown to an OD$_{600}$ of 0.12. Cultivation was carried out in a pressure-resistant 500 ml glass bottle with a premixed gas mixture composed of 67% H$_2$, 33% CO$_2$, in an open water bath shaker at 37° C., 150 rpm and with aeration of 3 L/h for 24 h. Subsequently, the gas mixture was changed to one with the composition of 66.85% H$_2$, 33% CO$_2$ and 0.15% O$_2$ and the cells were further gassed for 67 h at 3 L/h. The gas entry into the medium was carried out by a Begasungsfritte with a pore size of 10 microns, which was placed in the middle of the reactors at a sparger. The cells were centrifuged, washed with 10 ml ATCC medium and centrifuged again. The gas entry into the medium was carried out by a filter with a pore size of 10 microns, which was placed in the middle of the reactors. The cells were centrifuged, washed with 10 ml of ATCC medium and centrifuged again.

For the production culture many of washed cells from the preculture of *C. ljungdahlii* were transferred into 200 mL of ATCC medium with about 400 mg/L L-cysteine hydrochloride and grown to an OD$_{600}$ of 0.1. Cultivation was carried out in a pressure-resistant 500 ml glass bottle with a premixed gas mixture composed of 66.85% H$_2$, 33% CO$_2$ and 0.15% O$_2$, in an open water bath shaker at 37° C., 150 rpm and with aeration of 3 L/h for 113 h. The gas entry into the medium was carried out by a filter with a pore size of 10 microns, which was placed in the middle of the reactors. When sampling each 5 ml sample was removed for determination of OD$_{600}$, pH and the product range. The determination of the product concentration was performed by semi-quantitative 1H-NMR spectroscopy. As an internal quantification standard sodium trimethylsilylpropionate served (T (M) SP).

In the period from 89 h to 113 h there was no recognizable cell growth shown. The OD$_{600}$ was stagnated at 0.29, corresponding to a growth rate µ=0 h$^{-1}$. The concentration of acetate increased slightly during this time from 89.4 mg/L to 86.9 mg/L and the concentration of ethanol decreased from 16.2 mg/L to 11.9 mg/L.

Example 3

Culture of *Clostridium ljungdahlii* in Log Phase in the Presence of Synthesis Gas Comprising CO$_2$ and 0.15% Oxygen

*C. ljungdahlii* was fed H$_2$ and CO$_2$ out of the feed-through gas phase and formed acetate and ethanol. For the cultivation, pressure-resistant glass bottle that can be sealed airtight with a butyl rubber stopper were used. All cultivation steps, where *C. ljungdahlii* cells were involved were carried out under anaerobic conditions.

For cell culture of *C. ljungdahlii* 5 mL Cryoculture was cultured anaerobically in 500 ml of medium (ATCC 1754 medium: pH 6.0; 20 g/L MES; 1 g/L yeast extract, 0.8 g/L NaCl, 1 g/L NH$_4$Cl, 0.1 g/L KCl, 0.1 g/L KH$_2$PO$_4$, 0.2 g/L MgSO$_4$×7 H$_2$O; 0.02 g/L CaCl$_2$×2H$_2$O; 20 mg/L nitrilotriacetic acid 10 mg/L MnSO$_4$×H$_2$O; 8 mg/L (NH$_4$)$_2$Fe(SO$_4$)$_2$×6 H$_2$O; 2 mg/L CoCl$_2$×6 H$_2$O; 2 mg/L ZnSO$_4$×7 H$_2$O; 0.2 mg/L CuCl$_2$×2 H$_2$O; 0.2 mg/L Na$_2$MoO$_4$×2 H$_2$O; 0.2 mg/L NiCl$_2$×6 H$_2$O; 0.2 mg/L Na$_2$SeO$_4$; 0.2 mg/L Na$_2$WO$_4$×2 H$_2$O; 20 µg/L d-Biotin, 20 µg/L folic acid, 100 g/L pyridoxine-HCl; 50 µg/L thiamine-HCl×H$_2$O; 50 µg/L riboflavin; 50 µg/L nicotinic acid, 50 µg/L Ca-pantothenate; 1 µg/L vitamin B12; 50 µg/L p-aminobenzoate; 50 µg/L lipoic acid, approximately 67.5 mg/L NaOH) with about 400 mg/L L-cysteine hydrochloride and 400 mg/L Na$_2$S×9H$_2$O. Cultivation was carried chemolithoautotrophically in a flameproof 1 L glass bottle with a premixed gas mixture composed of 67% H$_2$, 33% CO$_2$ in an open water bath shaker at 37° C., 100 rpm and a fumigation of 3 L/h for 72 h. The gas entry into the medium was carried out by a filter with a pore size of 10 microns, and was mounted in the middle of the reactor, at a gassing tube. The cells were centrifuged, washed with 10 ml ATCC medium and centrifuged again.

For the main culture many washed cells from the growth culture of *C. ljungdahlii* were transferred into 500 mL of ATCC medium with about 400 mg/L L-cysteine hydrochloride and grown to an OD$_{600}$ of 0.1. Cultivation was carried out in a pressure-resistant 1 L glass bottle with a premixed gas mixture composed of 66.85% H$_2$, 33% CO$_2$, 0.15% O$_2$ in an open water bath shaker at 37° C., 150 rpm and with aeration of 1 L/h for 45 h. The gas entry into the medium was carried out by a filter with a pore size of 10 microns, which was placed in the middle of the reactors. When sampling each 5 ml sample was removed for determination of OD$_{600}$ nm, pH and the product range. The determination of the product concentration was performed by semi-quantitative 1H-NMR spectroscopy. As an internal quantification standard sodium trimethylsilylpropionate served (T (M) SP).

There was significant cell growth shown during the cultivation period, evidenced by an increase in OD$_{600}$ nm of 0.10 to 0.54, corresponding to a growth rate p=0.037 h$^{-1}$. The concentration of acetate increased at the same time from 9.6 mg/L to 3,304 mg/L and the concentration of ethanol from 2.2 mg/L to 399 mg/L.

Example 4

Culture of *Clostridium ljungdahlii* in Log Phase in the Presence of Synthesis Gas Comprising CO and 0.1% Oxygen

*C. ljungdahlii* was autotrophically cultivated in complex medium with synthesis gas, consisting of CO, $H_2$ and $CO_2$ in the presence of oxygen in order to produce acetate and ethanol.

A complex medium was used consisting of 1 g/L $NH_4Cl$, 0.1 g/L KCl, 0.2 g/L $MgSO_4 \times 7\ H_2O$, 0.8 g/L NaCl, 0.1 g/L $KH_2PO_4$, 20 mg/L $CaCl_2 \times 2\ H_2O$, 20 g/L MES, 1 g/L yeast extract, 0.4 g/L L-cysteine-HCl, 0.4 g/L $Na_2S \times 9H_2O$, 20 mg/L nitrilotriacetic acid, 10 mg/L $MnSO_4 \times H_2O$, 8 mg/L $(NH_4)_2Fe(SO_4)_2 \times 6\ H_2O$, 2 mg/L $CoCl_2 \times 6\ H_2O$, 2 mg/L $ZnSO_4 \times 7\ H_2O$, 0.2 mg/L $CuCl_2 \times 2\ H_2O$, 0.2 mg/L $Na_2MoO_4 \times 2\ H_2O$, 0.2 mg/L $NiCl_2 \times 6\ H_2O$, 0.2 mg/L $Na_2SeO_4$, 0.2 mg/L $Na_2WO_4 \times 2\ H_2O$, 20 µg/L biotin, 20 µg/L folic acid, 100 µg/L pyridoxine-HCl, 50 µg/L thiamine-HCl×$H_2O$, 50 µg/L riboflavin, 50 µg/L nicotinic acid, 50 µL Ca-pantothenoic acid, 1 µg/L vitamin B12, 50 µg/L p-aminobenzoic acid, 50 µg/L lipoic acid.

The autotrophic cultivation was performed in 500 mL medium in a 1 L serum bottle that was continuously gassed with synthesis gas consisting of 67.7% CO, 3.5% $H_2$ and 15.6% $CO_2$ at a rate of 3.6 L/h. The gas was introduced into the liquid phase by a microbubble disperser with a pore diameter of 10 µm. The serum bottle was continuously shaken in an open water bath Innova 3100 from New Brunswick Scientific at 37° C. and a shaking rate of 120 $min^{-1}$.

pH was not controlled.

At the beginning of the experiment, *C. ljungdahlii* was inoculated with an $OD_{600}$ of 0.1 with autotrophically grown cells on $H_2/CO_2$. Therefore, *C. ljungdahlii* was grown in complex medium under continuous gassing with synthesis gas consisting of 67% $H_2$ and 33% $CO_2$ at a rate of 3 L/h in 1 L serum bottles with 500 mL complex medium. Above described medium was also used for this cultivation. The gas was introduced into the liquid phase by a microbubble disperser with a pore diameter of 10 µm. The serum bottle was continuously shaken in an open water bath Innova 3100 from New Brunswick Scientific at 37° C. and a shaking rate of 150 $min^{-1}$. The cells were harvested in the logarithmic phase with an $OD_{600}$ of 0.49 and a pH of 5.03 by anaerobic centrifugation (4500 $min^{-1}$, 4300 g, 20° C., 10 min). The supernatant was discarded and the pellet was resuspended in 10 mL of above described medium. This cell suspension was then used to inoculate the cultivation experiment. Gas phase concentration of carbon monoxide was measured sampling of the gas phase and offline analysis by an gas chromatograph GC 6890N of Agilent Technologies Inc. with an thermal conductivity detector. Gas phase concentration of oxygen was measured by a trace oxygen dipping probe from PreSens Precision Sensing GmbH. Oxygen concentration was measured by fluorescence quenching, whereas the degree of quenching correlates to the partial pressure of oxygen in the gas phase. Oxygen measurement indicated a concentration of 0.1% vol of $O_2$ in the used synthesis gas.

During the experiment samples of 5 mL were taken for the determination of $OD_{600}$, pH and product concentrations. The latter were determined by quantitative $^1$H-NMR-spectroscopy.

After inoculation of *C. ljungdahlii*, cells began to grow with a growth rate µ of 0.062 $h^{-1}$ and continuously produced acetate up to a concentration of 6.2 g/L after 94.5 hours. Concomitant to the production of acetate, ethanol was produced in a lower rate compared to the production of acetate up to a concentration of 1 g/L after 94.5 hours.

TABLE 1 results of example 4

| Process time, h | pH | OD600 | Acetate, mg/L | Ethanol, mg/L |
|---|---|---|---|---|
| 0.0 | 6.15 | 0.10 | 18 | n.d. |
| 18.0 | 5.97 | 0.69 | 973 | 97 |
| 42.5 | 5.20 | 1.50 | | |
| 66.0 | 4.67 | 1.95 | 5368 | 966 |
| 94.5 | 4.54 | 1.77 | 6187 | 1070 |

(n.d. = not detected)

Example 5

Growth and Acetate Production by *Clostridium ljungdahlii* on Synthesis Gas with 2% Oxygen For the biotransformation of hydrogen and carbon dioxide to acetic acid the homoacetogenic bacterium *Clostridium ljungdahlii* was cultivated on synthesis gas with oxygen. All cultivation steps were carried out under anaerobic conditions in pressure-resistant glass bottles that can be closed airtight with a butyl rubber stopper.

For the preculture 500 ml medium (ATCC1754-medium: pH=6.0; 20 g/L MES; 1 g/L yeast extract, 0.8 g/L NaCl; 1 g/L $NH_4Cl$; 0.1 g/L KCl; 0.1 g/L $KH_2PO_4$; 0.2 g/L $MgSO_4 \times 7\ H_2O$; 0.02 g/L $CaCl_2 \times 2\ H_2O$; 20 mg/L nitrilotriacetic acid; 10 mg/L $MnSO_4 \times H_2O$; 8 mg/L $(NH_4)_2Fe(SO_4)_2 \times 6\ H_2O$; 2 mg/L $CoCl_2 \times 6\ H_2O$; 2 mg/L $ZnSO_4 \times 7\ H_2O$; 0.2 mg/L $CuCl_2 \times 2\ H_2O$; 0.2 mg/L $Na_2MoO_4 \times 2\ H_2O$; 0.2 mg/L $NiCl_2 \times 6\ H_2O$; 0.2 mg/L $Na_2SeO_4$; 0.2 mg/L $Na_2WO_4 \times 2\ H_2O$; 20 µg/L d-biotin; 20 µg/L folic acid; 100 µg/L pyridoxine-HCl; 50 µg/L thiamine-HCl×$H_2O$; 50 µg/L riboflavin; 50 µg/L nicotinic acid; 50 µg/L Ca-pantothenate; 1 µg/L vitamin $B_{12}$; 50 µg/L p-aminobenzoate; 50 µg/L lipoic acid; approx. 67.5 mg/L NaOH) with additional 400 mg/L L-cysteine-hydrochlorid and 400 mg/L $Na_2S \times 9H_2O$ were inoculated with 5 mL of a frozen cryo stock of *C. ljungdahlii*. The chemolithoautotrophic cultivation was carried out in a 1 L pressure-resistant glass bottle at 37° C., 100 rpm and a ventilation rate of 3 L/h with a premixed gas with 67% $H_2$, 33% $CO_2$ in an open water bath shaker for 72 h. The gas was discharged into the medium through a sparger with a pore size of 10 µm, which was mounted in the center of the reactors. Culturing was carried out with no pH control.

After the precultivation, the cell suspension was centrifuged (10 min, 4200 rpm) and the pellet was washed with 10 ml medium and centrifuged again. For the main culture, as many washed cells from the preculture as necessary for an $OD_{600nm}$ of 0.1 were transferred in 200 mL medium with additional 400 mg/L L-cysteine-hydrochlorid. The chemolithoautotrophic cultivation was carried out in a 250 mL pressure-resistant glass bottles at 37° C., 150 rpm and a ventilation rate of 1 L/h with a premixed gas with 65% $H_2$, 33% $CO_2$, 2% $O_2$ in an open water bath shaker for 47 h. The gas was discharged into the medium through a sparger with a pore size of 10 µm, which was mounted in the center of the reactors. Culturing was carried out with no pH control. During cultivation several 5 mL samples were taken to determinate $OD_{600nm}$, pH and product formation. The determination of the product concentrations was performed by semiquantitative 1H-NMR spectroscopy. As an internal quantification standard sodium trimethylsilylpropionate (T(M)SP) was used. Also the dissolved oxygen in the cultivation medium was measured online by oxygen dipping probes (PSt6 with Oxy4Trace, Presens, Germany).

During the cultivation period cell growth was observed by an increase of the $OD_{600nm}$ from 0.11 to 0.32, which correlates with a growth rate of $\mu=0.022$ h$^{-1}$. The concentration of acetate increased from 8 mg/L to 91 mg/L, an increase of the ethanol concentration was not observed. Over the cultivation period the dissolved oxygen concentration varied between 0.06 and 0.15 mg/L.

In a similar technical setting with the same parameters (medium composition, volume, bottle, gas, ventilation rate, temperature, shaking frequency), but without cells in the medium, a dissolved oxygen concentration of 0.50 mg/L was measured.

Example 6

Growth and Acetate Production by *Clostridium ljungdahlii* on Synthesis Gas with 0.15% Oxygen For the biotransformation of hydrogen and carbon dioxide to acetic acid the homoacetogenic bacterium *Clostridium ljungdahlii* was cultivated on synthesis gas with oxygen. All cultivation steps were carried out under anaerobic conditions in pressure-resistant glass bottles that can be closed airtight with a butyl rubber stopper.

For the preculture 500 ml medium (ATCC 1754-medium: pH=6.0; 20 g/L MES; 1 g/L yeast extract, 0.8 g/L NaCl; 1 g/L NH$_4$Cl; 0.1 g/L KCl; 0.1 g/L KH$_2$PO$_4$; 0.2 g/L MgSO$_4\times$7H$_2$O; 0.02 g/L CaCl$_2\times$2 H$_2$O; 20 mg/L nitrilotriacetic acid; 10 mg/L MnSO$_4\times$H$_2$O; 8 mg/L (NH$_4$)$_2$Fe(SO$_4$)$_2\times$6 H$_2$O; 2 mg/L CoCl$_2\times$6 H$_2$O; 2 mg/L ZnSO$_4\times$7 H$_2$O; 0.2 mg/L CuCl$_2\times$2 H$_2$O; 0.2 mg/L Na$_2$MoO$_4\times$2 H$_2$O; 0.2 mg/L NiCl$_2\times$6 H$_2$O; 0.2 mg/L Na$_2$SeO$_4$; 0.2 mg/L Na$_2$WO$_4\times$2 H$_2$O; 20 µg/L d-biotin; 20 µg/L folic acid; 100 µg/L pyridoxine-HCl; 50 µg/L thiamine-HClxH$_2$O; 50 µg/L riboflavin; 50 µg/L nicotinic acid; 50 µg/L Ca-pantothenate; 1 µg/L vitamin B$_{12}$; 50 µg/L p-aminobenzoate; 50 µg/L lipoic acid; approx. 67.5 mg/L NaOH) with additional 400 mg/L L-cysteine-hydrochlorid and 400 mg/L Na$_2$S×9H$_2$O were inoculated with 5 mL of a frozen cryo stock of *C. ljungdahlii*. The chemolithoautotrophic cultivation was carried out in a 1 L pressure-resistant glass bottle at 37° C., 100 rpm and a ventilation rate of 3 L/h with a premixed gas with 67% H$_2$, 33% CO$_2$ in an open water bath shaker for 72 h. The gas was discharged into the medium through a sparger with a pore size of 10 µm, which was mounted in the center of the reactors. Culturing was carried out with no pH control.

After the precultivation, the cell suspension was centrifuged (10 min, 4200 rpm) and the pellet was washed with 10 ml medium and centrifuged again. For the main culture, as many washed cells from the preculture as necessary for an $OD_{600nm}$ of 0.1 were transferred in 200 mL medium with additional 400 mg/L L-cysteine-hydrochlorid. The chemolithoautotrophic cultivation was carried out in a 250 mL pressure-resistant glass bottles at 37° C., 150 rpm and a ventilation rate of 1 L/h with a premixed gas with 66.85% H$_2$, 33% CO$_2$, 0.15% O$_2$ in an open water bath shaker for 47 h. The gas was discharged into the medium through a sparger with a pore size of 10 µm, which was mounted in the center of the reactors. Culturing was carried out with no pH control. During cultivation several 5 mL samples were taken to determinate $OD_{600nm}$, pH and product formation. The determination of the product concentrations was performed by semiquantitative 1H-NMR spectroscopy. As an internal quantification standard sodium trimethylsilylpropionate (T(M)SP) was used. Also the dissolved oxygen in the cultivation medium was measured online by oxygen dipping probes (PSt6 with Oxy4Trace, Presens, Germany).

During the cultivation period cell growth was observed by an increase of the $OD_{600nm}$ from 0.10 to 0.45, which correlates with a growth rate of $\mu=0.032$ The concentration of acetate increased from 7 mg/L to 2347 mg/L and the concentration of ethanol increased from 2 mg/L to 319 mg/L. Over the whole cultivation period the dissolved oxygen concentration was 0.00 mg/L.

In a similar technical setting with the same parameters (medium composition, volume, bottle, gas, ventilation rate, temperature, shaking frequency), but without cells in the medium, a dissolved oxygen concentration of 0.03 mg/L was measured.

Example 7

Co-Cultivation of *Clostridium ljungdahlii* and *Clostridium kluyveri* in Defined Medium on Hydrogen and Carbon Dioxide

*C. ljungdahlii* as first organism was autotrophically cultivated in defined medium in order to produce acetate and ethanol. After a given time, *C. kluyveri* as second organism was then inoculated in the same reactor for the conversion of acetate and ethanol to buyrate and hexanoate. In the following, *C. ljungdahlii* then converts butyrate to butanol.

A defined medium was used for the co-cultivation of both microorganisms consisting of 2 g/L (NH$_4$)$_2$HPO$_4$, 0.2 g/L NaCl, 0.15 g/l KCl, 1 g/l KOH, 0.5 g/L MgCl$_2\times$6 H$_2$O, 0.2 g/L CaCl$_2\times$2 H$_2$O, 15 mg/L FeCl$_2\times$4 H$_2$O, 0.4 g/L L-cysteine-HCl, 0.4 g/L Na$_2$S×9H$_2$O, 3 mg/L boric acid, 2 mg/L CoCl$_2\times$6 H$_2$O, 1 mg/L ZnSO$_4\times$7 H$_2$O, 0.3 mg/L Na$_2$MoO$_4\times$2 H$_2$O, 0.3 mg/L MnSO$_4\times$H$_2$O, 0.2 mg/L NiCl$_2\times$6 H$_2$O, 0.1 mg/L CuCl$_2\times$2 H$_2$O, 0.1 mg/L Na$_2$SeO$_3$, 106 µg/L biotin, 5 µg/L folic acid, 2.5 µg/L pyridoxine-HCl, 266 µg/L thiamine-HClxH$_2$O, 12.5 µg/L riboflavin, 12.5 µg/L nicotinic acid, 413 µg/L Ca-pantothenoic acid, 12.5 µg/L vitamin B12, 12.5 µg/L p-aminobenzoic acid, 15 µg/L lipioic acid.

The autotrophic cultivation was performed in 250 mL defined medium in a 500 mL serum bottle that was continuously gassed with synthesis gas consisting of 67% H$_2$ and 33% CO$_2$ at a rate of 1 L/h. The gas was introduced into the liquid phase by a microbubble disperser with a pore diameter of 10 µm. The serum bottle was continuously shaken in an open water bath Innova 3100 from New Brunswick Scientific at 37° C. and a shaking rate of 150 min$^{-1}$. The pH was held in a range of pH 5.0-6.5 by continuous addition of an anaerobic stock solution of KOH (40 g/L).

At the beginning of the experiment, *C. ljungdahlii* was inoculated with an $OD_{600}$ of 0.1 with autotrophically grown cells. Therefore, *C. ljungdahlii* was grown in complex medium under continuous gassing with synthesis gas consisting of 67% H$_2$ and 33% CO$_2$ at a rate of 3 L/h in 1 L serum bottles with 500 mL complex medium. A complex medium was used consisting of 1 g/L NH$_4$Cl, 0.1 g/L KCl, 0.2 g/L MgSO$_4\times$7 H$_2$O, 0.8 g/L NaCl, 0.1 g/L KH$_2$PO$_4$, 20 mg/L CaCl$_2\times$2 H$_2$O, 20 g/L MES, 1 g/L yeast extract, 0.4 g/L L-cysteine-HCl, 0.4 g/L Na$_2$S×9H$_2$O, 20 mg/L nitrilotriacetic acid, 10 mg/L MnSO$_4\times$H$_2$O, 8 mg/L (NH$_4$)$_2$Fe(SO$_4$)$_2\times$6 H$_2$O, 2 mg/L CoCl$_2\times$6 H$_2$O, 2 mg/L ZnSO$_4\times$7 H$_2$O, 0.2 mg/L CuCl$_2\times$2 H$_2$O, 0.2 mg/L Na$_2$MoO$_4\times$2 H$_2$O, 0.2 mg/L NiCl$_2\times$6 H$_2$O, 0.2 mg/L Na$_2$SeO$_4$, 0.2 mg/L Na$_2$WO$_4\times$2 H$_2$O, 20 µg/L biotin, 20 µg/L folic acid, 100 µg/L pyridoxine-HCl, 50 µg/L thiamine-HClxH$_2$O, 50 µg/L riboflavin, 50 µg/L nicotinic acid, 50 µg/L Ca-pantothenoic acid, 1 µg/L vitamine B 12, 50 µg/L p-aminobenzoic acid, 50

µg/L lipoic acid. The gas was introduced into the liquid phase by a microbubble disperser with a pore diameter of 10 µm. The serum bottle was continuously shaken in an open water bath Innova 3100 from New Brunswick Scientific at 37° C. and a shaking rate of 150 min$^{-1}$. The cells were harvested in the late-logarithmic phase with an OD$_{600}$ of 0.67 and a pH of 4.69 by anaerobic centrifugation (4500 min$^{-1}$, 4300 g, 20° C., 10 min). The supernatant was discarded and the pellet was resuspended in 10 mL of above described defined medium. This cell suspension was then used to inoculate the co-culture experiment.

Parallel to that, C. kluyveri were grown heterotrophically in 200 mL complex medium in 500 mL serum bottles on acetate and ethanol. A complex medium was used consisting of 0.25 g/L NH$_4$Cl, 0.2 g/L MgSO$_4$×7 H$_2$O, 0.31 g/L K$_2$HPO$_4$, 0.23 g/L KH$_2$PO$_4$, 2.5 g/L NaHCO$_3$, 1 g/L yeast extract, 10 g/L K-acetate, 20 g/l ethanol, 0.25 g/L L-cysteine-HCl, 1.5 mg/L FeCl$_2$×4 H$_2$O, 70 µg/L ZnCl$_2$×7 H$_2$O, 100 µg/L MnCl$_2$×4 H$_2$O, 6 µg/L boric acid, 190 µg/L CoCl$_2$×6 H$_2$O, 2 µg/L CuCl$_2$×6 H$_2$O, 24 µg/L NiCl$_2$×6 H$_2$O, 36 µg/L Na$_2$MoO$_4$×2 H$_2$O, 3 µg/L Na$_2$SeOO$_3$×5 H$_2$O, 4 µg/L Na$_2$WO$_4$×2 H$_2$O, 100 µg/L vitamine B12, 80 µg/L p-aminobenzoic acid, 20 µg/L biotin, 200 µg/L nicotinic acid, 100 µg/L Ca-pantothenoic acid, 300 µg/L pyridoxine-HCl, 200 µg/L thiamine-HCl×H$_2$O. The serum bottle was continuously shaken in an open water bath Innova 3100 from New Brunswick Scientific at 37° C. and a shaking rate of 100 min$^{-1}$. The cells were harvested in the late-logarithmic phase with an OD$_{600}$ of 0.81 and a pH of 5.96 by anaerobic centrifugation (4500 min$^{-1}$, 4300 g, 20° C., 10 min). The supernatant was discarded and the pellet was resuspended in 10 mL of above described defined medium. This cell suspension was then used to inoculate the co-culture experiment with an OD$_{600}$ of 0.2 after 96 hours of the running experiment.

During the experiment samples of 5 mL were taken for the determination of OD$_{600}$, pH and product concentrations. The latter were determined by quantitative $^1$H-NMR-spectroscopy.

After inoculation of C. ljungdahlii, cells began to grow and continuously produced acetate. Concomitant to the production of acetate, ethanol was produced in a lower rate compared to the production of acetate. After 96 hours C. kluyveri was then inoculated into the reactor a decrease of ethanol concentration was measured in the following experiment. The simultaneous production of butyrate (max. 1163 mg/L) and hexanoate (max. 136 mg/L) was then measured in the following 113 hours of the experiment. Parallel to the production of butyrate by C. kluyveri, C. ljungdahlii converted butyrate to butanol to a maximum concentration of 20 mg/L butanol at the end of the experiment.

TABLE 2

Results of Example 7

| Process time, h | pH | OD600 | NMR-analytics | | | | | |
|---|---|---|---|---|---|---|---|---|
| | | | Acetate, mg/L | Ethanol, mg/L | Butyrate, mg/L | n-Butanol, mg/L | Hexanoate, mg/L | Hexanol, mg/L |
| 0.0 | 6.37 | 0.11 | 4 | 2 | n.d. | n.d. | n.d. | n.d. |
| 19.5 | 5.49 | 0.12 | 818 | 10 | n.d. | n.d. | n.d. | n.d. |
| 40.3 | 5.49 | 0.21 | 1930 | 51 | n.d. | n.d. | n.d. | n.d. |
| 63.8 | 5.10 | 0.43 | 5005 | 160 | n.d. | n.d. | n.d. | n.d. |
| 79.5 | 5.85 | 0.49 | 8444 | 260 | n.d. | n.d. | n.d. | n.d. |
| 95.0 | 5.95 | 0.58 | 8984 | 291 | n.d. | n.d. | n.d. | n.d. |
| 96.0 | 5.90 | 0.78 | 9299 | 316 | 16 | n.d. | 23 | n.d. |
| 121.5 | 6.28 | 0.71 | 11030 | 9 | 801 | 10 | 81 | n.d. |
| 142.3 | 6.29 | 0.71 | 12238 | 8 | 934 | 14 | 87 | n.d. |
| 160.3 | 6.30 | 0.67 | 13096 | 9 | 1006 | 16 | 103 | n.d. |
| 185.5 | 6.28 | 0.57 | 16860 | 13 | 1143 | 17 | 134 | n.d. |
| 209.0 | 6.23 | 0.52 | 19275 | 17 | 1163 | 16 | 136 | n.d. |
| 234.0 | 5.82 | 0.42 | 18368 | 19 | 991 | 15 | 108 | n.d. |
| 259.3 | 5.72 | 0.34 | 18744 | 20 | 1005 | 15 | 116 | n.d. |

(n.d. = not detected)

Example 8

Co-Cultivation of Clostridium ljungdahlii and Clostridium kluyveri in Complex Medium with CO-Containing Gas C. ljungdahlii as first organism was autotrophically cultivated in complex medium in order to produce acetate and ethanol. After a given time, C. kluyveri as second organism was then inoculated in the same reactor for the conversion of acetate and ethanol to buyrate and hexanoate. In the following, C. ljungdahlii then converts butyrate to butanol and hexanoate to hexanol.

A complex medium was used for the co-cultivation of both microorganisms consisting of 1 g/L NH$_4$Cl, 0.1 g/L KCl, 0.2 g/L MgSO$_4$×7 H$_2$O, 0.8 g/L NaCl, 0.1 g/L KH$_2$PO$_4$, 20 mg/L CaCl$_2$×2 H$_2$O, 20 g/L MES, 1 g/L yeast extract, 0.4 g/L L-cysteine-HCl, 0.4 g/L Na$_2$S×9H$_2$O, 20 mg/L nitrilotriacetic acid, 10 mg/L MnSO$_4$×H$_2$O, 8 mg/L (NH$_4$)$_2$Fe(SO$_4$)$_2$×6 H$_2$O, 2 mg/L CoCl$_2$×6 H$_2$O, 2 mg/L ZnSO$_4$×7 H$_2$O, 0.2 mg/L CuCl$_2$×2 H$_2$O, 0.2 mg/L Na$_2$MoO$_4$×2 H$_2$O, 0.2 mg/L NiCl$_2$×6 H$_2$O, 0.2 mg/L Na$_2$SeO$_4$, 0.2 mg/L Na$_2$WO$_4$×2 H$_2$O, 20 µg/L biotin, 20 µg/L folic acid, 100 µg/L pyridoxine-HCl, 50 µg/L thiamine-HCl×H$_2$O, 50 µg/L riboflavin, 50 µg/L nicotinic acid, 50 µg/L Ca-pantothenoic acid, 1 µg/L vitamin B12, 50 µg/L p-aminobenzoic acid, 50 µg/L lipoic acid.

The autotrophic cultivation was performed in 500 mL complex medium in a 1 L serum bottle that was continuously gassed with synthesis gas consisting of 5% H$_2$, 25% CO$_2$, 25% CO and 45% N$_2$ at a rate of ~12 L/h (≥0.5 ppm). The gas was introduced into the liquid phase by a microbubble disperser with a pore diameter of 10 µm. The serum bottle was continuously shaken in an open water bath Innova 3100 from New Brunswick Scientific at 37° C. and a shaking rate of 120 min$^{-1}$. The pH was not controlled during this experiment.

At the beginning of the experiment, C. ljungdahlii was inoculated with an OD$_{600}$ of 0.1 with autotrophically grown cells. Therefore, C. ljungdahlii was grown in above described complex medium under continuous gassing with synthesis gas consisting of 67% $H_2$ and 33% $CO_2$ at a rate of 3 L/h in 1 L serum bottles with 500 mL complex medium. The gas was introduced into the liquid phase by a microbubble disperser with a pore diameter of 10 μm. The serum bottle was continuously shaken in an open water bath Innova 3100 from New Brunswick Scientific at 37° C. and a shaking rate of 150 $min^{-1}$. The cells were harvested in the late-logarithmic phase with an $OD_{600}$ of 0.51 and a pH of 5.04 by anaerobic centrifugation (4500 $min^{-1}$, 4300 g, 20° C., 10 min). The supernatant was discarded and the pellet was resuspended in 10 mL of above described complex medium. This cell suspension was then used to inoculate the co-culture experiment.

Parallel to that, C. kluyveri was grown heterotrophically in 200 mL complex medium in 500 mL serum bottles on acetate and ethanol. A complex medium was used consisting of 0.25 g/L $NH_4Cl$, 0.2 g/L $MgSO_4 \times 7$ $H_2O$, 0.31 g/L $K_2HPO_4$, 0.23 g/L $KH_2PO_4$, 2.5 g/L $NaHCO_3$, 1 g/L yeast extract, 10 g/L K-acetate, 20 g/l ethanol, 0.25 g/L L-cysteine-HCl, 1.5 mg/L $FeCl_2 \times 4$ $H_2O$, 70 μg/L $ZnCl_2 \times 7$ $H_2O$, 100 μg/L $MnCl_2 \times 4$ $H_2O$, 6 μg/L boric acid, 190 μg/L $CoCl_2 \times 6$ $H_2O$, 2 μg/L $CuCl_2 \times 6$ $H_2O$, 24 μg/L $NiCl_2 \times 6$ $H_2O$, 36 μg/L $Na_2MoO_4 \times 2$ $H_2O$, 3 μg/L $Na_2SeOO_3 \times 5$ $H_2O$, 4 μg/L $Na_2WO_4 \times 2$ $H_2O$, 100 μg/L vitamin B12, 80 μg/L p-aminobenzoic acid, 20 μg/L biotin, 200 μg/L nicotinic acid, 100 μg/L Ca-pantothenoic acid, 300 μg/L pyridoxine-HCl, 200 μg/L thiamine-HCl×$H_2O$. The serum bottle was continuously shaken in an open water bath Innova 3100 from New Brunswick Scientific at 37° C. and a shaking rate of 100 $min^{-1}$. The cells were harvested in the late-logarithmic phase with an $OD_{600}$ of 0.54 and a pH of 6.60 by anaerobic centrifugation (4500 $min^{-1}$, 4300 g, 20° C., 10 min). The supernatant was discarded and the pellet was resuspended in 10 mL of above described complex medium. This cell suspension was then used to inoculate the co-culture experiment after 240 hours of the running experiment.

During the experiment samples of 5 mL were taken for the determination of $OD_{600}$, pH and product concentrations. The latter were determined by quantitative $^1$H-NMR-spectroscopy.

After inoculation of C. ljungdahlii, cells began to grow and continuously produced acetate to a concentration of ~3 g/L and ethanol to a concentration of ~0.5 g/L after 71 hours. In the following time course of the experiment, acetate was completely converted to ethanol up to a concentration of 4.8 g/L after 240 hours. At a process time of 240 hours, C. kluyveri was then inoculated into the reactor. As this organism needs acetate besides ethanol as substrate, simultaneous to the inoculation of C. kluyveri approximately 3 g/L acetate (in the form of Na-acetate) were brought into the reactor anaerobically. In the following time course of the experiment, the production of butyrate and hexanoate up to concentrations of 1.6 g/L each were measured. Parallel to the production of butyrate and hexanoate by C. kluyveri, C. ljungdahlii converted butyrate to butanol to a maximum concentration of 690 mg/L butanol and converted hexanaote to hexanol to a maximum concentration of 1478 mg/L hexanol.

TABLE 3

Results of Example 8

| | | | NMR-analytics | | | | | |
|---|---|---|---|---|---|---|---|---|
| Process time, h | pH | OD600 | Acetate, mg/L | Ethanol, mg/L | Butyrate, mg/L | n-Butanol, mg/L | Hexanoate, mg/L | Hexanol, mg/L |
| 0.0 | 6.13 | 0.11 | 26 | 3 | n.d. | n.d. | n.d. | n.d. |
| 18.0 | 5.89 | 0.55 | 1063 | 18 | n.d. | n.d. | n.d. | n.d. |
| 42.0 | 5.58 | 1.02 | 2353 | 79 | n.d. | n.d. | n.d. | n.d. |
| 71.3 | 5.31 | 1.34 | 3081 | 534 | n.d. | n.d. | n.d. | n.d. |
| 117.5 | 5.39 | 1.78 | 2612 | 1946 | n.d. | n.d. | n.d. | n.d. |
| 162.0 | 5.87 | 1.88 | 665 | 4153 | n.d. | n.d. | n.d. | n.d. |
| 192.0 | 6.02 | 1.85 | 43 | 4747 | n.d. | n.d. | n.d. | n.d. |
| 240.0 | 6.03 | 1.19 | 28 | 4805 | n.d. | n.d. | n.d. | n.d. |
| 240.0 | 6.03 | 1.17 | 3209 | 4775 | 134 | n.d. | 46 | n.d. |
| 258.0 | 6.24 | 1.22 | 1078 | 1727 | 46 | 522 | 1380 | 457 |
| 283.5 | 6.49 | 1.24 | 331 | 112 | 1380 | 690 | 1590 | 1478 |
| 330.0 | 6.50 | 0.80 | 343 | 110 | 1590 | 603 | 1344 | 1165 |

(n.d. = not detected)

Example 9

Growth and Production of Acetate and other Compounds by Clostridium carboxidivorans on Synthesis Gas with 0.05% Oxygen For the biotransformation of hydrogen and carbon dioxide to acetic acid and other compounds the homoacetogenic bacterium Clostridium carboxidivorans was cultivated on synthesis gas with oxygen. All cultivation steps were carried out under anaerobic conditions in pressure-resistant glass bottles that can be closed airtight with a butyl rubber stopper.

For the preculture 500 ml medium (ATCC1754-medium: pH=6.0; 20 g/L MES; 1 g/L yeast extract, 0.8 g/L NaCl; 1 g/L $NH_4Cl$; 0.1 g/L KCl; 0.1 g/L $KH_2PO_4$; 0.2 g/L $MgSO_4 \times 7$ $H_2O$; 0.02 g/L $CaCl_2 \times 2$ $H_2O$; 20 mg/L nitrilotriacetic acid; 10 mg/L $MnSO_4 \times H_2O$; 8 mg/L $(NH_4)_2Fe(SO_4)_2 \times 6$ $H_2O$; 2 mg/L $CoCl_2 \times 6$ $H_2O$; 2 mg/L $ZnSO_4 \times 7$ $H_2O$; 0.2 mg/L $CuCl_2 \times 2$ $H_2O$; 0.2 mg/L $Na_2MoO_4 \times 2$ $H_2O$; 0.2 mg/L $NiCl_2 \times 6$ $H_2O$; 0.2 mg/L $Na_2SeO_4$; 0.2 mg/L $Na_2WO_4 \times 2$ $H_2O$; 20 μg/L d-biotin; 20 μg/L folic acid; 100 μg/L pyridoxine-HCl; 50 μg/L thiamine-HCl×$H_2O$; 50 μg/L riboflavin; 50 μg/L nicotinic acid; 50 μg/L Ca-pantothenate; 1 μg/L vitamin $B_{12}$; 50 μg/L p-aminobenzoate; 50 μg/L lipoic acid; approx. 67.5 mg/L NaOH) with additional 400 mg/L L-cysteine-hydrochloride and 400 mg/L $Na_2S \times 9H_2O$ were inoculated with 5 mL of a frozen cryo stock of C. carboxidivorans. The chemolithoautotrophic cultivation was carried out in a 1 L pressure-resistant glass bottle at 37° C., 100 rpm and a ventilation rate of 3 L/h with a premixed gas with 60% $H_2$, 20% $CO_2$, and 20% CO in an open water bath shaker for 71 h. The gas was discharged into the medium through a sparger with a pore size of 10 μm, which was mounted in the center of the reactors. Culturing was carried out with no pH control.

After the precultivation, the cell suspension was centrifuged (10 min, 4200 rpm) and the pellet was resuspended in fresh medium. For the main culture, as many cells from the preculture as necessary for an $OD_{600nm}$ of 0.2 were transferred in 200 mL complex medium (ATCC1754) and parallel in 200 ml mineral medium (DM4-medium: pH=6.00, 0.5 g/L $MgCl_2 \times 6\ H_2O$, 0.2 g/L $CaCl_2 \times 2\ H_2O$, 15 mg/L $FeCl_2 \times 4\ H_2O$, 2 g/L $(NH_4)H_2PO_4$, 0.2 g/L NaCl, 0.15 g/L KCl, 3 mg/L $H_3BO_3$, 2 mg/L $CoCl_2 \times 6\ H_2O$, 1 mg/L $ZnSO_4 \times 7\ H_2O$, 300 μg/L $Na_2MoO_4 \times 2\ H_2O$, 300 μg/L $MnSO_4 \times H_2O$, 200 μg/L $NiCl_2 \times 6\ H_2O$, 100 μg/L $CuCl_2 \times 2\ H_2O$, 100 μg/L $Na_2SeO_3$, 106 μg/L d-biotin, 5 μg/L folic acid, 2.5 μg/L pyridoxine-HCl, 266 μg/L thiamine-HCl, 12.5 μg/L riboflavin, 12.5 μg/L nicotinic acid, 413 μg/L Ca-pantothenate, 12.5 μg/L vitamin $B_{12}$, 12.5 μg/L p-aminobenzoate, 15.0 μg/L lipoic acid, approx. 1.3 g/L KOH), with additional 400 mg/L L-cysteine-hydrochloride each. The chemolithoautotrophic cultivation was carried out in a 1 L pressure-resistant glass bottle at 37° C., 150 rpm and a ventilation rate of 1 L/h with a premixed gas with 66.95% $H_2$, 33% $CO_2$, and 0.05% $O_2$ in an open water bath shaker for 40 h. The gas was discharged into the head space through a sparger with a pore size of 10 μm, which was mounted in the center of the reactors. Culturing was carried out with no pH control. During cultivation several 5 mL samples were taken to determinate $OD_{600nm}$, pH and product formation. The determination of the product concentrations was performed by semiquantitative 1H-NMR spectroscopy. As an internal quantification standard sodium trimethylsilylpropionate (T(M)SP) was used. Also the dissolved oxygen in the cultivation medium was measured online by oxygen dipping probes (PSt6 with Oxy4Trace, Presens, Germany).

During the cultivation period cell growth was observed in complex medium by an increase of the $OD_{600nm}$ from 0.20 to 0.36, which correlates with a growth rate of p=0.015 $h^{-1}$. In mineral medium, the $OD_{600nm}$ decreased from 0.20 to 0.19. In complex medium the concentration of acetate increased from 29 mg/L to 280 mg/L, for ethanol from 3 mg/L to 82 mg/L, for butyrate from 0 mg/L to 29 mg/L and for butanol from 0 mg/L to 10 mg/L. In mineral medium the concentration of acetate increased from 25 mg/L to 110 mg/L, for ethanol from 3 mg/L to 5 mg/L and for butyrate from 0 mg/L to 2 mg/L. Over the whole cultivation period the dissolved oxygen concentration in both cultures was 0.00 mg/L. In a similar technical setting with the same parameters (medium composition, volume, bottle, gas, ventilation rate, temperature, shaking frequency), but without cells in the medium, a dissolved oxygen concentration of 0.01 mg/L was measured in both media.

Example 10

Growth and Production of Acetate and Ethanol by *Clostridium autoethanogenum* on Synthesis Gas with 0.05% Oxygen For the biotransformation of hydrogen and carbon dioxide to acetic acid and ethanol the homoacetogenic bacterium *Clostridium autoethanogenum* was cultivated on synthesis gas with oxygen. All cultivation steps were carried out under anaerobic conditions in pressure-resistant glass bottles that can be closed airtight with a butyl rubber stopper.

For the preculture 500 ml medium (ATCC1754-medium: pH=6.0; 20 g/L MES; 1 g/L yeast extract, 0.8 g/L NaCl; 1 g/L $NH_4Cl$; 0.1 g/L KCl; 0.1 g/L $KH_2PO_4$; 0.2 g/L $MgSO_4 \times 7\ H_2O$; 0.02 g/L $CaCl_2 \times 2\ H_2O$; 20 mg/L nitrilotriacetic acid; 10 mg/L $MnSO_4 \times H_2O$; 8 mg/L $(NH_4)_2Fe(SO_4)_2 \times 6\ H_2O$; 2 mg/L $CoCl_2 \times 6\ H_2O$; 2 mg/L $ZnSO_4 \times 7\ H_2O$; 0.2 mg/L $CuCl_2 \times 2\ H_2O$; 0.2 mg/L $Na_2MoO_4 \times 2\ H_2O$; 0.2 mg/L $NiCl_2 \times 6\ H_2O$; 0.2 mg/L $Na_2SeO_4$; 0.2 mg/L $Na_2WO_4 \times 2\ H_2O$; 20 μg/L d-biotin; 20 μL folic acid; 100 μg/L pyridoxine-HCl; 50 μg/L thiamine-HCl×$H_2O$; 50 μg/L riboflavin; 50 μg/L nicotinic acid; 50 μg/L Ca-pantothenate; 1 μg/L vitamin $B_{12}$; 50 μg/L p-aminobenzoate; 50 μg/L lipoic acid; approx. 67.5 mg/L NaOH) with additional 400 mg/L L-cysteine-hydrochloride and 400 mg/L $Na_2S \times 9H_2O$ were inoculated with 5 mL of a frozen cryo stock of *C. autoethanogenum*. The chemolithoautotrophic cultivation was carried out in a 1 L pressure-resistant glass bottle at 37° C., 100 rpm and a ventilation rate of 3 L/h with a premixed gas with 67% $H_2$, 33% $CO_2$ in an open water bath shaker for 72 h. The gas was discharged into the medium through a sparger with a pore size of 10 μm, which was mounted in the center of the reactors. Culturing was carried out with no pH control.

After the precultivation, the cell suspension was centrifuged (10 min, 4200 rpm) and the pellet was resuspended in fresh medium. For the main culture, as many cells from the preculture as necessary for an $OD_{600nm}$ of 0.1 were transferred in 500 mL medium with additional 400 mg/L L-cysteine-hydrochlorid. The chemolithoautotrophic cultivation was carried out in a 1 L pressure-resistant glass bottle at 37° C., 150 rpm and a ventilation rate of 1 L/h with a premixed gas with 66.95% $H_2$, 33% $CO_2$, and 0.05% $O_2$ in an open water bath shaker for 41 h. The gas was discharged into the medium through a sparger with a pore size of 10 μm, which was mounted in the center of the reactors. Culturing was carried out with no pH control. During cultivation several 5 mL samples were taken to determinate $OD_{600nm}$, pH and product formation. The determination of the product concentrations was performed by semiquantitative 1H-NMR spectroscopy. As an internal quantification standard sodium trimethylsilylpropionate (T(M)SP) was used. Also the dissolved oxygen in the cultivation medium was measured online by oxygen dipping probes (PSt6 with Oxy4Trace, Presens, Germany).

During the cultivation, period cell growth was observed by an increase of the $OD_{600nm}$ from 0.08 to 0.76 in 41 h, which correlates with a growth rate of μ=0.054 $h^{-1}$. The concentration of acetate increased from 37 mg/L to 6600 mg/L and the concentration of ethanol increased from 4 mg/L to 120 mg/L. Over the whole cultivation period the dissolved oxygen concentration was 0.00 mg/L.

In a similar technical setting with the same parameters (medium composition, volume, bottle, gas, ventilation rate, temperature, shaking frequency), but without cells in the medium, a dissolved oxygen concentration of 0.01 mg/L was measured.

Example 11

Growth and Acetate Production by *Clostridium ljungdahlii* on Synthesis Gas with 0.6% Oxygen For the biotransformation of hydrogen and carbon dioxide to acetic acid the homoacetogenic bacterium *Clostridium ljungdahlii* was cultivated on synthesis gas with oxygen. All cultivation steps were carried out under anaerobic conditions in pressure-resistant glass bottles that can be closed airtight with a butyl rubber stopper.

For the preculture 500 ml medium (ATCC1754-medium: pH=6.0; 20 g/L MES; 1 g/L yeast extract, 0.8 g/L NaCl; 1 g/L $NH_4Cl$; 0.1 g/L KCl; 0.1 g/L $KH_2PO_4$; 0.2 g/L MgSO$_4$×7 H$_2$O; 0.02 g/L CaCl$_2$×2 H$_2$O; 20 mg/L nitrilotriacetic acid; 10 mg/L MnSO$_4$×H$_2$O; 8 mg/L (NH$_4$)$_2$Fe(SO$_4$)$_2$×6 H$_2$O; 2 mg/L CoCl$_2$×6 H$_2$O; 2 mg/L ZnSO$_4$×7 H$_2$O; 0.2 mg/L CuCl$_2$×2 H$_2$O; 0.2 mg/L Na$_2$MoO$_4$×2 H$_2$O; 0.2 mg/L NiCl$_2$×6 H$_2$O; 0.2 mg/L Na$_2$SeO$_4$; 0.2 mg/L Na$_2$WO$_4$×2 H$_2$O; 20 µg/L d-biotin; 20 µg/L folic acid; 100 µg/L pyridoxine-HCl; 50 µg/L thiamine-HCl×H$_2$O; 50 µg/L riboflavin; 50 µg/L nicotinic acid; 50 µg/L Ca-pantothenate; 1 µg/L vitamin B$_{12}$; 50 µg/L p-aminobenzoate; 50 µg/L lipoic acid; approx. 67.5 mg/L NaOH) with additional 400 mg/L L-cysteine-hydrochloride and 400 mg/L Na$_2$S×9H$_2$O were inoculated with 5 mL of a frozen cryo stock of *C. ljungdahlii*. The chemolithoautotrophic cultivation was carried out in a 1 L pressure-resistant glass bottle at 37° C., 100 rpm and a ventilation rate of 3 L/h with a premixed gas with 67% H$_2$, 33% CO$_2$ in an open water bath shaker for 72 h. The gas was discharged into the medium through a sparger with a pore size of 10 µm, which was mounted in the center of the reactors. Culturing was carried out with no pH control.

After the precultivation, the cell suspension was centrifuged (10 min, 4200 rpm) and the pellet was washed with 10 ml medium and centrifuged again. For the main culture, as many washed cells from the preculture as necessary for an OD$_{600nm}$ of 0.1 were transferred in 200 mL medium with additional 400 mg/L L-cysteine-hydrochloride. The chemolithoautotrophic cultivation was carried out in a 250 mL pressure-resistant glass bottles at 37° C., 150 rpm and a ventilation rate of 1 L/h with a premixed gas with 66.85% H$_2$, 33% CO$_2$, 0.6% O$_2$ in an open water bath shaker for 91 h. The gas was discharged into the medium through a sparger with a pore size of 10 µm, which was mounted in the center of the reactors. Culturing was carried out with no pH control. During cultivation several 5 mL samples were taken to determinate OD$_{600nm}$, pH and product formation. The determination of the product concentrations was performed by semiquantitative 1H-NMR spectroscopy. As an internal quantification standard sodium trimethylsilylpropionate (T(M)SP) was used. Also the dissolved oxygen in the cultivation medium was measured online by oxygen dipping probes (PSt6 with Oxy4Trace, Presens, Germany).

During the cultivation period cell growth was observed by an increase of the OD$_{600nm}$ from 0.10 to 0.16, which correlates with a growth rate of µ=5×10$^{-3}$. The concentration of acetate increased from 9 mg/L to 476 mg/L and the concentration of ethanol increased from 6 mg/L to 61 mg/L. Over the cultivation period the dissolved oxygen concentration was between 0.01 and 0.10 mg/L.

In a similar technical setting with the same parameters (medium composition, volume, bottle, gas, ventilation rate, temperature, shaking frequency), but without cells in the medium, a dissolved oxygen concentration of 0.15 mg/L was measured.

Example 12

Growth and Production of Acetate by *Acetobacterium woodii* on Synthesis Gas with Oxygen For the biotransformation of hydrogen and carbon dioxide to acetic acid the homoacetogenic bacterium *Acetobacterium woodii* is cultivated on synthesis gas with oxygen. All cultivation steps are carried out under anaerobic conditions in pressure-resistant glass bottles that can be closed airtight with a butyl rubber stopper. For the preculture 500 ml medium (ATCC 1754-medium: pH=6.0; 20 g/L MES; 1 g/L yeast extract, 0.8 g/L NaCl; 1 g/L NH$_4$Cl; 0.1 g/L KCl; 0.1 g/L KH$_2$PO$_4$; 0.2 g/L MgSO$_4$×7 H$_2$O; 0.02 g/L CaCl$_2$×2 H$_2$O; 20 mg/L nitrilotriacetic acid; 10 mg/L MnSO$_4$×H$_2$O; 8 mg/L (NH$_4$)$_2$Fe(SO$_4$)$_2$×6 H$_2$O; 2 mg/L CoCl$_2$×6 H$_2$O; 2 mg/L ZnSO$_4$×7 H$_2$O; 0.2 mg/L CuCl$_2$×2 H$_2$O; 0.2 mg/L Na$_2$MoO$_4$×2 H$_2$O; 0.2 mg/L NiCl$_2$×6 H$_2$O; 0.2 mg/L Na$_2$SeO$_4$; 0.2 mg/L Na$_2$WO$_4$×2 H$_2$O; 20 µg/L d-biotin; 20 µg/L folic acid; 100 µg/L pyridoxine-HC1; 50 µg/L thiamine-HC1×H$_2$O; 50 µg/L riboflavin; 50 µg/L nicotinic acid; 50 µg/L Ca-pantothenate; 1 µg/L vitamin B$_{12}$; 50 µg/L p-aminobenzoate; 50 µg/L lipoic acid; approx. 67.5 mg/L NaOH) with additional 400 mg/L L-cysteine-hydrochloride and 400 mg/L Na$_2$S×9H$_2$O are inoculated with 5 mL of a frozen cryo stock of *A. woodii*. The chemolithoautotrophic cultivation is carried out in a 1 L pressure-resistant glass bottle at 37° C., 100 rpm and a ventilation rate of 3 L/h with a premixed gas with 67% H$_2$, 33% CO$_2$ in an open water bath shaker for 72 h. The gas is discharged into the medium through a sparger with a pore size of 10 µm, which is mounted in the center of the reactors. Culturing is carried out with no pH control.

After the precultivation, the cell suspension is centrifuged (10 min, 4200 rpm) and the pellet is resuspended in fresh medium. For the main culture, as many cells from the preculture as necessary for an OD$_{600nm}$ of 0.1 are transferred in 500 mL medium with additional 400 mg/L L-cysteine-hydrochlorid. The chemolithoautotrophic cultivation is carried out in a 1 L pressure-resistant glass bottle at 37° C., 150 rpm and a ventilation rate of 1 L/h with a premixed gas with 66.95% H$_2$, 33% CO$_2$, 0.05% O$_2$ in an open water bath shaker for 41 h. The gas is discharged into the medium through a sparger with a pore size of 10 µm, which is mounted in the center of the reactors. Culturing is carried out with no pH control. During cultivation several 5 mL samples are taken to determinate OD$_{600nm}$, pH and product formation. The determination of the product concentrations is performed by semiquantitative 1H-NMR spectroscopy. As an internal quantification standard sodium trimethylsilylpropionate (T(M)SP) is used. Also the dissolved oxygen in the cultivation medium is measured online by oxygen dipping probes (PSt6 with Oxy4Trace, Presens, Germany).

During the cultivation period cell growth is observed by an increase of the OD$_{600nm}$. Also the concentration of acetate increases.

In a similar technical setting with the same parameters (medium composition, volume, bottle, gas, ventilation rate, temperature, shaking frequency), but without cells in the medium, a dissolved oxygen concentration of 0.01 mg/L is measured.

European patent application 15152866.8 filed Jan. 28, 2015, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A reaction mixture for producing ethanol and/or acetate from a carbon source in an aerobic condition, the mixture comprising:
   a first acetogenic microorganism in an exponential growth phase;
   free oxygen; and
   a second acetogenic microorganism in a stationary phase, wherein the first acetogenic microorganism and the second acetogenic microorganism are capable of converting the carbon source to the acetate and/or ethanol.

2. The reaction mixture according to claim 1, wherein the first and second acetogenic microorganisms are each independently selected from the group consisting of *Acetoan-*

*aerobium notera* (ATCC 35199), *Acetonema longum* (DSM 6540), *Acetobacterium carbinolicum* (DSM 2925), *Acetobacterium malicum* (DSM 4132), *Acetobacterium* species no. 446, *Acetobacterium wieringae* (DSM 1911), *Acetobacterium woodii* (DSM 1030), *Alkalibaculum bacchi* (DSM 22112), *Archaeoglobus fulgidus* (DSM 4304), *Blautia producta* (DSM 2950), *Butyribacterium methylotrophicum* (DSM 3468), *Clostridium aceticum* (DSM 1496), *Clostridium autoethanogenum* (DSM 10061, DSM 19630 and DSM 23693), *Clostridium carboxidivorans* (DSM 15243), *Clostridium coskatii* (ATCC no. PTA-10522), *Clostridium drakei* (ATCC BA-623), *Clostridium formicoaceticum* (DSM 92), *Clostridium glycolicum* (DSM 1288), *Clostridium ljungdahlii* (DSM 13528), *Clostridium ljungdahlii* C-01 (ATCC 55988), *Clostridium ljungdahlii* ERI-2 (ATCC 55380), *Clostridium ljungdahlii* O-52 (ATCC 55989), *Clostridium mayombei* (DSM 6539), *Clostridium methoxybenzovorans* (DSM 12182), *Clostridium neopropionicum* sp, *Clostridium ragsdalei* (DSM 15248), *Clostridium scatologenes* (DSM 757), *Clostridium* species ATCC 29797, *Desulfotomaculum kuznetsovii* (DSM 6115), *Desulfotomaculum thermobezoicum* subsp. *thermosyntrophicum* (DSM 14055), *Eubacterium limosum* (DSM 20543), *Methanosarcina acetivorans* C2A (DSM 2834), *Moorella* sp. HUC22-1, *Moorella thermoacetica* (DSM 521), *Moorella thermoautotrophica* (DSM 1974), *Oxobacter pfennigii* (DSM 322), *Sporomusa aerivorans* (DSM 13326), *Sporomusa ovata* (DSM 2662), *Sporomusa silvacetica* (DSM 10669), *Sporomusa sphaeroides* (DSM 2875), *Sporomusa termitida* (DSM 4440), and *Thermoanaerobacter kivui* (DSM 2030).

3. The reaction mixture according to claim 1, wherein the first acetogenic microorganism has a growth rate of 0.01 to 2 $h^{-1}$.

4. The reaction mixture according to claim 1, wherein the first acetogenic microorganism has an $OD_{600}$ of 0.01 to 2.

5. The reaction mixture according to claim 1, wherein the reaction mixture is made in the aerobic condition by supplying continuous gas flow comprising from 0.000005% to 1% by volume of oxygen to the reaction mixture.

6. The reaction mixture according to claim 1, wherein the carbon source comprises CO.

7. The reaction mixture according to claim 2, wherein the first acetogenic microorganism has a growth rate of 0.01 to 2 $h^{-1}$.

8. The reaction mixture according to claim 2, wherein the first acetogenic microorganism has an $OD_{600}$ of 0.01 to 2.

9. The reaction mixture according to claim 3, wherein the first acetogenic microorganism has an $OD_{600}$ of 0.01 to 2.

10. The reaction mixture according to claim 2, wherein the reaction mixture is made in the aerobic condition by supplying continuous gas flow comprising from 0.000005% to 1% by volume of oxygen to the reaction mixture.

11. The reaction mixture according to claim 3, wherein the reaction mixture is made in the aerobic condition by supplying continuous gas flow comprising from 0.000005% to 1% by volume of oxygen to the reaction mixture.

12. The reaction mixture according to claim 2, wherein the carbon source comprises CO.

13. The reaction mixture according to claim 1, wherein the reaction mixture is made in the aerobic condition by supplying continuous gas flow comprising about 0.015% by volume of oxygen to the reaction mixture.

* * * * *